(12) United States Patent
Suster et al.

(10) Patent No.: US 11,408,844 B2
(45) Date of Patent: Aug. 9, 2022

(54) DIELECTRIC SENSING TO CHARACTERIZE HEMOSTATIC DYSFUNCTION

(71) Applicants: CASE WESTERN RESERVE UNIVERSITY, Cleveland, OH (US); UNIVERSITY OF PITTSBURGH, Pittsburgh, PA (US)

(72) Inventors: Michael Suster, Cleveland Heights, OH (US); Pedram Mohseni, Highland Heights, OH (US); Anirban Sen Gupta, Cleveland, OH (US); Matthew David Neal, Sewickley, PA (US); Ujjal Didar Singh Sekhon, Cleveland, OH (US); Sanjay Pitamber Ahuja, Cleveland Heights, OH (US); Sina Pourang, Cleveland Heights, OH (US); Debnath Maji, Ellsworth, ME (US)

(73) Assignees: CASE WESTERN RESERVE UNIVERSITY, Cleveland, OH (US); THE UNITED STATES GOVERNMENT AS REPRESENTED BY THE DEPARTMENT OF VETERAN AFFAIRS, Washington, DC (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 244 days.

(21) Appl. No.: 16/837,704

(22) Filed: Apr. 1, 2020

(65) Prior Publication Data
US 2020/0319128 A1 Oct. 8, 2020

Related U.S. Application Data

(60) Provisional application No. 62/828,286, filed on Apr. 2, 2019.

(51) Int. Cl.
*G01N 27/22* (2006.01)
*G01N 27/02* (2006.01)
*G01N 33/49* (2006.01)

(52) U.S. Cl.
CPC ......... *G01N 27/221* (2013.01); *G01N 27/026* (2013.01); *G01N 27/226* (2013.01); *G01N 33/4905* (2013.01)

(58) Field of Classification Search
CPC .. G01N 27/221; G01N 27/026; G01N 27/226; G01N 33/4905
See application file for complete search history.

(56) References Cited

U.S. PATENT DOCUMENTS 4,686,857 A 8/1987 Kato
4,765,179 A 8/1988 Fuller et al.
(Continued)

FOREIGN PATENT DOCUMENTS

CN 101720432 A 6/2010
CN 102680523 A 9/2012
(Continued)

OTHER PUBLICATIONS

Applicant: University of Case Western Reserve; "Dielectric Sensing for Sample Characterization"; Chinese Office Action; dated Mar. 8, 2021; 8 pgs.
(Continued)

*Primary Examiner* — Farhana A Hoque
(74) *Attorney, Agent, or Firm* — Tarolli, Sundheim, Covell & Tummino LLP

(57) ABSTRACT

As one example, an apparatus includes a dielectric microsensor comprising a microfluidic chamber that includes a capacitive sensing structure, the microfluidic chamber including a fluid input port to receive a volume of a blood sample. A bioactive agent is disposed within the
(Continued)

chamber to interact with the volume of the blood sample received in the microfluidic chamber. A transmitter provides an input radio frequency (RF) signal to an RF input of the dielectric microsensor. A receiver receives an output RF signal from an RF output of the dielectric microsensor. A computing device that computes dielectric permittivity values of the sample that vary over a time interval based on the output RF signal, the computing device to provide an assessment of hemostatic dysfunction and associated coagulopathy based on the dielectric permittivity values.

29 Claims, 10 Drawing Sheets

(56) References Cited

U.S. PATENT DOCUMENTS

| | | | |
|---|---|---|---|
| 4,884,457 | A | 12/1989 | Hatton |
| 5,042,299 | A | 8/1991 | Wells |
| 6,255,954 | B1 | 7/2001 | Brown et al. |
| 6,362,632 | B1 | 3/2002 | Livingston |
| 6,467,358 | B1 | 10/2002 | Nishi et al. |
| 6,922,064 | B2 | 7/2005 | Halalay et al. |
| D558,086 | S | 12/2007 | Herber |
| 7,541,004 | B2 | 6/2009 | Niksa et al. |
| 8,735,163 | B2 | 5/2014 | Hayahi et al. |
| 8,776,246 | B2 | 7/2014 | Allegri et al. |
| 8,884,771 | B2 | 11/2014 | Cooke et al. |
| 9,194,859 | B2 | 11/2015 | Emeric et al. |
| 2003/0090276 | A1 | 5/2003 | Van Der Weide et al. |
| 2004/0147032 | A1 | 7/2004 | Martin et al. |
| 2004/0237657 | A1 | 12/2004 | Xie et al. |
| 2010/0235107 | A1 | 9/2010 | Fukumura et al. |
| 2010/0251816 | A1 | 10/2010 | Bahorich et al. |
| 2010/0252452 | A1 | 10/2010 | Newman et al. |
| 2011/0234240 | A1 | 9/2011 | Yager |
| 2012/0055810 | A1 | 3/2012 | Zhou |
| 2012/0112850 | A1 | 5/2012 | Kim et al. |
| 2012/0238026 | A1 | 9/2012 | Hayashi et al. |
| 2013/0204202 | A1 | 8/2013 | Trombly et al. |
| 2013/0296847 | A1 | 11/2013 | Germain et al. |
| 2014/0114592 | A1 | 4/2014 | Eilertsen |
| 2015/0346125 | A1 | 12/2015 | Hayashi et al. |
| 2015/0346131 | A1 | 12/2015 | Mohseni et al. |
| 2016/0011170 | A1 | 1/2016 | Brun et al. |
| 2019/0029555 | A1* | 1/2019 | Suster .................... A61B 5/145 |

FOREIGN PATENT DOCUMENTS

| | | |
|---|---|---|
| EP | 2 375 244 A1 | 10/2011 |
| JP | 2012194087 A | 10/2012 |
| WO | 2010109317 A1 | 9/2010 |
| WO | 2014/141845 A1 | 9/2014 |
| WO | 2016/040490 A1 | 3/2016 |

OTHER PUBLICATIONS

Applicant: Case Western Reserve University; European Patent Application No. EP17739159.6; European Office Action dated Apr. 30, 2021; 6 pgs.
Kumiko Sakurai, "A microengineered vascularized bleeding model that integrates the principal components of hemostasis"; Article, Nature Communications; www.nature.com/naturecommunications; Feb. 6, 2018; 9 pgs.
John B. Holcomb, M.D., et al., "Causes of Death in U.S. Special Operations Forces in the Global War on Terrorism 2001-2004"; Original Articles, Annals of Surgery, vol. 245, No. 6, Jun. 2007, 6 pgs.
Sixu Chen, MM., et al.; "Progress on combat damage control resuscitation/surgery and its application in the Chinese People's Liberation Army"; Review Article, J. Trauma Acute Care Surg, vol. 87, No. 4, Jan. 1988, 7 pgs.
Richard L. Simmons, Capt., MC, USAR, et al., "Annals of Surgery", vol. 169 No. 4, Aug. 3, 1968, 28 pgs.
Donald H. Jenkins, et al., "Trauma Hemostasis and Oxygenation Research Position paper on Remote Damage Control Resuscitation: Definitions, Current Practice, and Knowledge Gaps", SHOCK, vol. 41, Supplement 1, Jan. 8, 2014, pp. 3-12.
Ronald Chang, et al., "Advances in the understanding of trauma-induced coagulopathy", Review Article—Case Western Reserve University, Jun. 30, 2020, 7 pgs.
Jeffrey W. Simmons, et al., "Trauma-Induced Coagulopathy"; Publication, Anesthesia for Trauma, Curr Anesthesiol Rep; 11 pgs.
Kathleen E. Brummel-Ziedins, et al., "Global Assays of Hemostasis"; Publication NIH Public Access, Sep. 21, 2014; 16 pgs.
M. Levi, et al., "A critical appraisal of point-of-care coagulation testing in critically ill patients", Article, Journal of Thrombosis and Haemostasis, 13: 1960-1967; May 25, 2015; 8 pgs.
Ying Zheng, et al., "Microvascular platforms for the study of platelet-vessel wall interactions"; Review Article, Thrombosis Research, Dec. 30, 2013; 7 pgs.
Ryan W. Muthard, et al., "Fibrin, y-Fibrinogen, and Transclot Pressure Gradient Control Hemostatic Clot Growth During Human Blood Flow Over a Collagen/Tissue Factor Wound"; http://ahajournals.org, Jun. 30, 2020; 10 pgs.
Lucas H. Ting, et al., "Contractile forces in platelet aggregates under microfluidic shear gradients reflect platelet inhibition and bleeding risk", Article, Nature Communications; www.nature.com/naturecommunications; Mar. 13, 2019; 10 pgs.
D. Maji, et al., "Assessment of whole blood coagulation with a microfluidic dielectric sensor", Journal of Thrombosis and Haemostasis, Sep. 26, 2017; 7 pgs.
Debnath Maji, et al., "ClotChip: A Microfluidic Dielectric Sensor for Point-of-Care Assessment of Hemostasis"; Manuscript, HHS Public Access; IEEE Trans Biomed Circuits Syst; Dec. 11, 2017; 22 pgs.
Extended European Search Report for Application No. 17739159.6, dated Aug. 2, 2019.
Maji Debnath et al., "Monitoring time course of human whole blood coagulation using a microfluidic dielectric sensor with a 3D capacitive structure", Aug. 25, 2015, pp. 5904-5907.
Yoshihito Hayashi et al., "Principles of Dielectric Blood Coagulometry as a Comprehensive Coagulation Test", Analytical Chemistry, vol. 87, No. 19, Sep. 14, 2015.
Supplementary European Search Report for Application No. 17739159.6, dated Aug. 21, 2019.
Ahmed A. Helmy, et al., "A 1-8-GHz Miniaturized Spectroscopy System for Permittivity Detection and Mixture Characterization of Organic Chemicals", IEEE Transactions on Microwave Theory and Techniques, vol. 60, No. 12, Dec. 2012, pp. 4157-4170.
Ahmed A. Helmy, et al., "A Self-Sustained CMOS Microwave Chemical Sensor Using a Frequency Synthesizer", IEEE Journal of Solid-State Circuits, vol. 47, No. 10, Oct. 2012, pp. 2467-2483.
Ahmed A. Helmy, et al., "Complex Permittivity Detection of Organic Chemicals and Mixtures Using a 0.5-3-GHz Miniaturized Spectroscopy System", IEEE Transactions on Microwave Theory and Techniques, vol. 61, No. 12, Dec. 2013, pp. 4646-4659.
Ahmei C. Sabuncu, et al., "Microfluidic impedance spectroscopy as a tool for quantitative biology and biotechnology", Biomicrofluidics 6, 034103 (2012).
Arun Manickam, et al., "A CMOS Electrochemical Impedance Spectroscopy (EIS) Biosensor Array", IEEE Transactions on Biomedical Circuits and Systems, vol. 4, No. 6, Dec. 2010, pp. 379-390.
Chao Yang, et al., "Compact Low-Power Impedance-to-Digital Converter for Sensor Array Microsystems", IEEE Journal of Solid-State Circuits, vol. 44, No. 10, Oct. 2009, pp. 2844-2855.
Ebrahim Ghafar-Zadeh, et al., "A Hybrid Microfluidic/CMOS Capacitive Sensor Dedicated to Lab-on-Chip Applications", IEEE Transactions on Biomedical Circuits and Systems, vol. 1, No. 4, Dec. 2007, pp. 270-277.
G. R. Facer, et al., "Dielectric spectroscopy for bioanalysis: From 40 Hz to 26.5 GHz in a microfabricated wave guide", Applied Physics Letters, vol. 78, No. 7, Feb. 12, 2001, pp. 996-998.

(56) References Cited

OTHER PUBLICATIONS

Hamed Mazhab-Jafari, et al., "16-Channel CMOS Impedance Spectroscopy DNA Analyzer With Dual-Slope Multiplying ADCs", IEEE Transactions on Biomedical Circuits and Systems, vol. 6, No. 5, Oct. 2012, pp. 468-478.
James C. Booth, et al., "Quantitative Permittivity Measurements of Nanoliter Liquid Volumes in Microfluidic Channels to 40 GHz", IEEE Transactions on Instrumentation and Measurement, vol. 59, No. 12, Dec. 2010, pp. 3279-3288.
Jun-Chau Chien, et al., "A 1-50 GHz Dielectric Spectroscopy Biosensor with Integrated Receiver Front-end in 65nm CMOS", 2013.
Jun-Chau Chien, et al., "A 6.S/11117.S/30-GHz High Throughput Interferometer-based Reactance Sensors using Injection-Locked Oscillators and Ping-Pong Nested Chopping", 2014 Symposium on VLSI Circuits Digest of Technical Papers.
Kang-Ho Lee, et al., "A CMOS Impedance Cytometer for 3D Flowing Single-Cell Real-Time Analysis ?S with Error Correction", 2012 IEEE International Solid-State Circuits Conference, pp. 304-306.
Katia Grenier, et al., "Integrated Broadband Microwave and Microfluidic Sensor Dedicated to Bioengineering", IEEE Transactions on Microwave Theory and Techniques, vol. 57, No. 12, Dec. 2009, pp. 3246-3253.
Khalil Heileman, et al., "Dielectric spectroscopy as a viable biosensing tool for cell and tissue characterization and analysis", Biosensors and Bioelectronics, 49 (2013), pp. 348-359.
Masoud Moslehi Bajestan, et al., "A 0.62-1 OGHz CMOS Dielectric Spectroscopy System for Chemical/Biological Material Characterization", 2014.
Mehran Bakhshiani, et al., "A 9 MHz-2.4 GHz Fully Integrated Transceiver IC for a Microfluidic-CMOS Platform Dedicated to Miniaturized Dielectric Spectroscopy", IEEE Transactions on Biomedical Circuits and Systems, vol. 9, No. 6, Dec. 2015, pp. 849-861.
Mehran Bakhshiani, et al., "A Broadband Sensor Interface IC for Miniaturized Dielectric Spectroscopy From MHz to GHz", IEEE Journal of Solid-State Circuits, vol. 49, No. 8, Aug. 2014.
Mehran Bakhshiani, et al., "A Microfluidic-CMOS Platform with 3D Capacitive Sensor and Fully Integrated Transceiver IC for Palmtop Dielectric Spectroscopy", 2015 IEEE International Solid-State Circuits Conference, pp. 386-388.
Michael A. Suster, et al., "A Circuit Model of Human Whole Blood in a Microfluidic Dielectric Sensor", IEEE Transactions on Circuits and Systems—II: Express Briefs, vol. 63, No. 12, Dec. 2016, pp. 1156-1160.
Michael A. Suster, et al., "An RF/Microwave Microfluidic Sensor Based on a 3D Capacitive Structure with a Floating Electrode for Miniaturized Dielectric Spectroscopy", 2014.
Michael A. Suster, et al., "An RF/Microwave Microfluidic Sensor Based on a Center-Gapped Microstrip Line for Miniaturized Dielectric Spectroscopy", 2013.
Michael A. Suster, et al., "An RF/Microwave Microfluidic Sensor for Miniaturized Dielectric Spectroscopy Based on Sensor Transmission Characteristics", 2015.
Milan Daphtary, et al., "Broadband Capacitive Sensor CMOS Interface Circuit for Dielectric Spectroscopy", ISCAS 2006, pp. 4285-4288.
Osama Elhadidy, et al., "A CMOS Fractional-PLL-Based Microwave Chemical Sensor With 1.5% Permittivity Accuracy" IEEE Transactions on Microwave Theory and Techniques, vol. 61, No. 9, Sep. 2013, pp. 3402-3416.
Osama Elhadidy, et al., "A Wide-Band Fully-Integrated CMOS Ring-Oscillator PLL-Based Complex Dielectric Spectroscopy System", IEEE Transactions on Circuits and Systems—I: Regular Papers, vol. 62, No. 8, Aug. 2015, pp. 1940-1949.
S S Stuchly, et al., "Microwave coplanar sensors for dielectric measurements", Meas. Sci. Technol. 9 (1998) pp. 1324-1329.
S. Gawad, et al., "Micromachined impedance spectroscopy flow cytometer for cell analysis and particle sizing", Lab an a Chip, 2001, 1, pp. 76-82.
Sanghyun Seo, et al., "High Frequency Wideband Permittivity Measurements of Biological Substances Using Coplanar Waveguides and Application to Cell Suspensions", 2008, pp. 915-918.
Mohseni, et al., "A Miniaturized Dielectric Blood Coagulometer"; Oct. 20, 2015.
Applicant: Case Western Reserve University; Japanese Patent Application No. 2018-536778, Filed Jan. 17, 2017; Entitled "Dielectric Sensing for Sample Characterization"; Chinese OA; dated Nov. 27, 2020.
Applicant: Case Western Reserve University; Chinese Patent Application No. 201780009585.5, Filed Jan. 17, 2017; Entitled "Dielectric Sensing for Sample Characterization"; Chinese OA; dated Aug. 5, 2020.

* cited by examiner

DIELECTRIC SENSING TO CHARACTERIZE HEMOSTATIC DYSFUNCTION

CROSS-REFERENCE TO RELATED APPLICATION

This application claims priority from U.S. provisional application No. 62/828,286, filed Apr. 2, 2019, and entitled DIELECTRIC SENSING TO CHARACTERIZE HEMOSTATIC DYSFUNCTION, which is incorporated herein by reference in its entirety.

TECHNICAL FIELD

This disclosure relates to dielectric sensing to characterize hemostatic dysfunction of a sample.

BACKGROUND

Traumatic hemorrhage, exsanguination and trauma-induced coagulopathy (TIC) are majorly implicated in morbidities and mortalities for both civilian and military populations, especially in the age group of 1-50. Detrimental effects of hemorrhage and TIC can happen within minutes to hours of injury, and need to be treated rapidly with hemorrhage control strategies, transfusion medicine and resuscitative surgeries. To guide these approaches, rapid 'point-of-injury' assessment of hemostatic dysfunction and associated coagulopathy is needed, but this presents severe challenges in the trauma patients, especially in pre-hospital and remote location scenarios (e.g., injured combat personnel in the field, civilian injuries at the roadside etc.).

For civilian and battlefield trauma, hemorrhage and the associated coagulopathy are the leading causes of "preventable death" due to the injury, and rates of death due to hemorrhage approach 50% of injured patients. Time is of the essence in preventing death due to bleeding, and as such, much of the prevention and resuscitation of bleeding is focused on pre-hospital care. For such patients, often a massive transfusion protocol (MTP) is recommended, which requires effective hematologic and coagulation profiling prior to and during transfusion. Currently, such profiling involves in-hospital tests of plasma coagulation status (e.g., by prothrombin time—PT), platelet function status (e.g., by aggregometry and platelet function analyzer (PFA)), and clot viscoelasticity status (e.g., by thromboelastography—TEG or rotational thromboelastometry—ROTEM), which are all separate instruments/tests. Therefore, these analyses take time, and in many cases of traumatic injury, access to a central laboratory with such analytic capabilities may not be possible in a timely manner.

SUMMARY

This disclosure relates to dielectric sensing to characterize hemostatic dysfunction of a sample, such as to assess trauma-induced coagulopathy (TIC).

As an example, an apparatus includes a dielectric microsensor comprising a microfluidic chamber that includes a capacitive sensing structure. The microfluidic chamber includes a fluid input port to receive a volume of a blood sample, and a bioactive agent is disposed within the microfluidic chamber to interact with the volume of the blood sample received in the microfluidic chamber. A transmitter is configured to provide an input radio frequency (RF) signal to an RF input of the dielectric microsensor. A receiver is configured to receive an output RF signal from an RF output of the dielectric micro sensor. A computing device is configured to compute dielectric permittivity values of the blood sample that vary over a time interval based on the output RF signal, and to provide an assessment of hemostatic dysfunction based on the dielectric permittivity values.

As another example, a method includes introducing a volume of at least one blood sample into a chamber between electrodes of a dielectric microsensor, the blood sample interacting with a bioactive agent within the chamber. The method also includes providing an input radio frequency (RF) signal to an input of the dielectric microsensor. The method also includes receiving an output RF signal from an output of the dielectric microsensor in response to the input RF signal. The output RF signal represents a measure of impedance of a volume of the blood sample disposed in the dielectric microsensor according to the interaction with the bioactive agent. The method also includes calculating dielectric permittivity values of the blood sample over a measurement time interval based on the output RF signal. The method also includes providing an assessment of hemostatic dysfunction based on analysis of the dielectric permittivity values.

DETAILED DESCRIPTION

Figure 1:
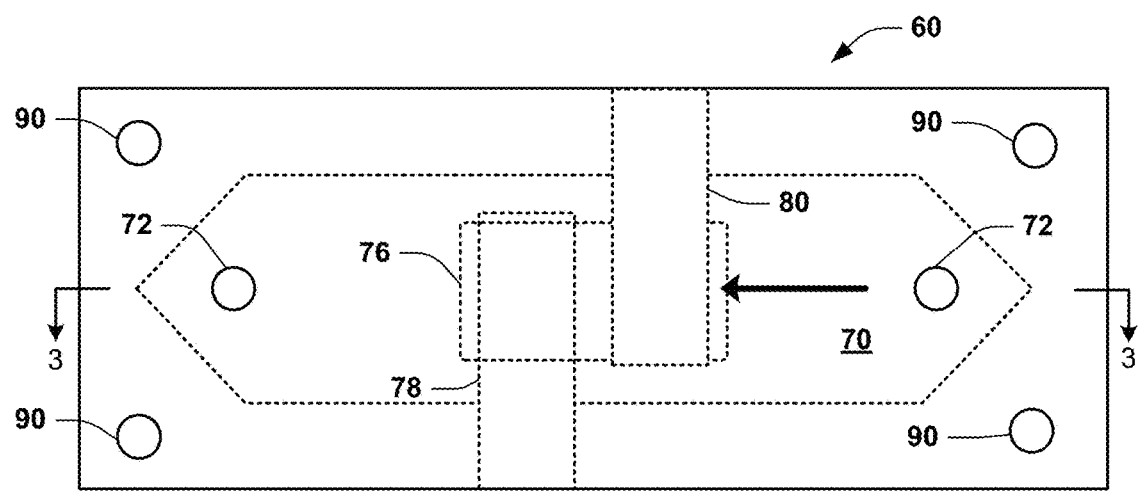
FIG. 1 depicts a top elevation of an example dielectric microsensor.

This disclosure relates to a dielectric microsensor apparatus and method to assess hemostatic dysfunction and the associated coagulopathy. The assessment is provided based on dielectric spectroscopy (DS) applied to one or more samples of blood. For example, a dielectric microsensor, associated interface electronics and computing device can be integrated in a portable apparatus (e.g., a handheld or desktop unit).

As an example, the microsensor includes a parallel-plate capacitive sensing structure based on a 3D gap with a floating electrode to extract the complex permittivity of a blood sample in a microfluidic chamber (e.g., a channel). In an example, two planar sensing electrodes are separated from a floating electrode through a microfluidic channel to form a 3D capacitive sensing area. As the blood sample is introduced into and/or passes through this area, the impedance of the sensor changes based upon the blood's dielectric permittivity. There can be any number of sensing chambers to analyze the blood sample in multiplexed fashion. One or more bioactive agents are disposed in at least one chamber to interact with the blood sample deterministically within such chamber. The bioactive agent may be adapted to promote, accelerate, or inhibit coagulation of the blood sample. In some examples, the contact surface of one or more electrodes of the sensing structure are configured (e.g., surface modified) to contain the bioactive agent, such as in the form of a coating or layer. Examples of some bioactive agents that may be utilized, individually or in combination, include collagen, fibrinogen, inorganic polyphosphate (PolyP), chitosan, kaolin, phosphatidylserine (PS), Adenosine 5'-diphosphate (ADP), thrombin receptor-activating peptide (TRAP), aprotinin, Tissue Factor (TF) and the like. As disclosed herein, the bioactive agents may be applied to a given electrode, to multiple electrodes or any other surface or surfaces within the fluidic chamber to be contacted by blood during DS operations. Alternatively, one or more bioactive agents may be otherwise introduced and/or mixed with the blood sample that is introduced into the fluidic chamber.

As one example, ADP, TRAP, and collagen may be applied to the surface of one or more electrodes to assess platelet response in whole blood. As another example, tissue factor, kaolin, and phosphatidylserine may be applied to the surface of one or more electrodes to assess coagulation factor response. In yet another example, aprotinin may be applied to the surface of one or more electrodes to assess hyperfibrinolytic state compared to a response on tissue factor-coated electrodes. Thus, microsensors having desired bioactive agents, such as disclosed herein, can be pre-configured to provide a set of sensors that may be operatively coupled to the sensing apparatus to assess different respective hemostatic dysfunctions. In an example, a selected sensor having a predetermined bioactive agent(s) may be placed in respective ones of a plurality of sensor-receiving slots in the apparatus to detect different respective cellular and non-cellular abnormalities in hemostasis in a given sample of blood that is placed into the sensor. In another example, multiple different sensors, each preconfigured with different bioactive agents, may be placed in respective ones of a plurality of sensor-receiving slots in the apparatus concurrently to detect different respective cellular and non-cellular abnormalities in hemostasis in a given sample of blood.

As disclosed herein, the apparatus can be configured to detect hemostatic dysfunction, such as may occur in trauma patients. For example, the apparatus is configured to perform dielectric coagulometry to detect hemostatic dysfunction and associated coagulopathy in trauma patient blood exposed to the bioactive agent and the permittivity profile will allow determination of deviations from a healthy blood coagulation profile. The apparatus may be implemented in a small-size, low-cost, disposable sensor using a miniscule volume (<10 µL) of whole blood. Moreover, the fully electronic technique of dielectric spectroscopy will enable the readout to be integrated into a small-size, portable, hand-held instrument, which is highly advantageous for both military and civilian first responders.

Figure 2:
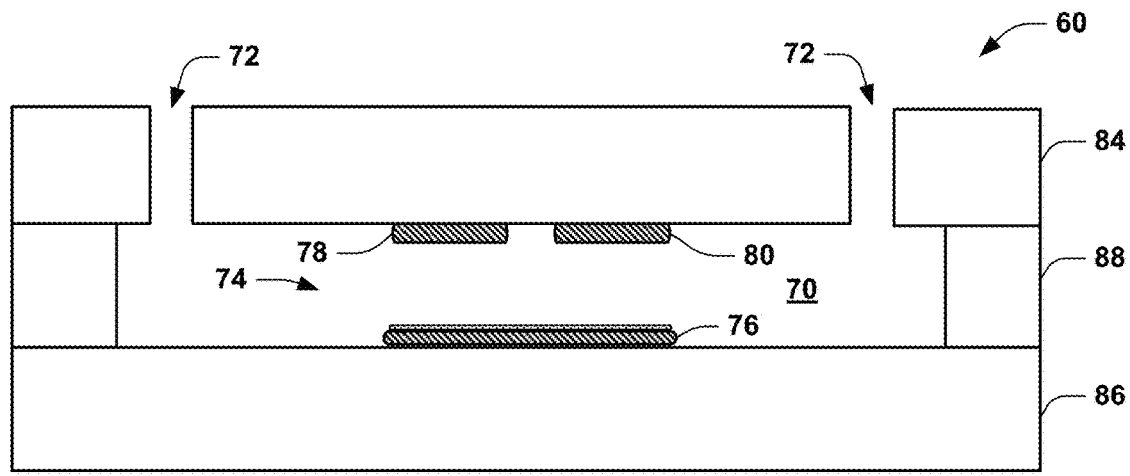
FIG. 2 depicts an example of the dielectric microsensor of FIG. 1 taken along the lines of 3-3.
Figure 3:
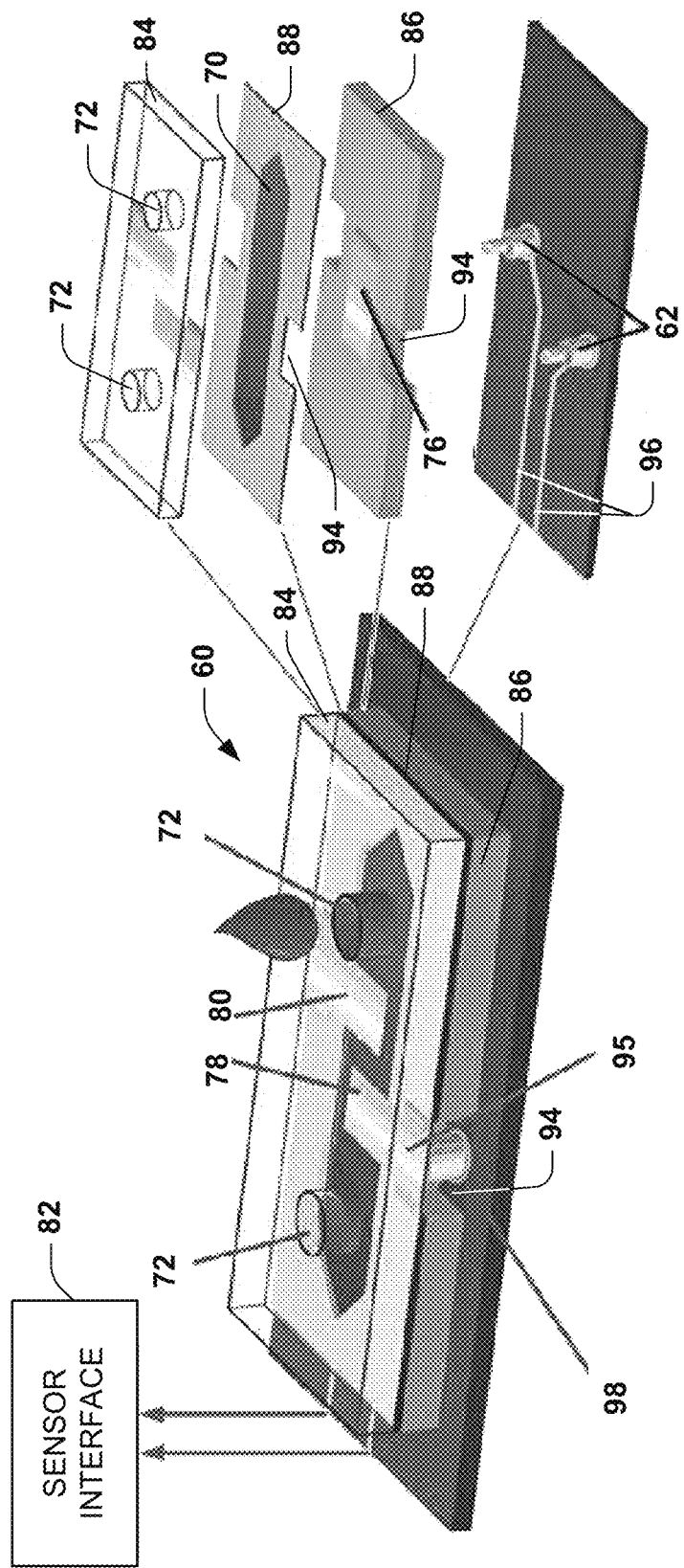
FIG. 3 is an assembly view of the example sensor of FIG. 2.

FIGS. 1, 2 and 3 demonstrate different views of an example of a three-dimensional dielectric microsensor 60. The microsensor 60 can be electrically coupled to a sensor interface system (see FIGS. 6 and 7) such as via electrical contact pins 62. Other types of connections (e.g., electrically conductive, optical fiber or wireless) could also be utilized to provide for bi-directional communication with respect to the microsensor apparatus 60.

In the example of FIGS. 1, 2 and 3, an interface system (e.g., corresponding to transmitter 222 of FIG. 6) 82 provides an RF input signal to an electrical input (e.g., corresponding to an electrode) 78 of the microsensor 60. The microsensor 60 includes circuitry having a complex admittance (e.g., capacitance) that varies as a function of dielectric permittivity of blood sample within a fluid channel 70, such as disclosed herein. The microsensor 60 includes an electrical output 80 that provides an RF output signal to the interface system (e.g., interface 214) via an output connection (e.g., a pin or other type of electrical connection) 62, which RF output signal varies as a function of time based on the input frequency and the dielectric permittivity of a sample under test (SUT). The microsensor 60 also includes a fluidic chamber (e.g., a channel) 70 into which a volume of an SUT (e.g., liquid or gas) can be introduced via ports 72 (e.g., inlet and outlet holes). For purposes of consistency of explanation, the following discussion presumes that the SUT is blood. Other types of biological fluid SUTs could be used in other examples.

The microsensor 60 includes a capacitive sensing structure 74 (see FIG. 2) disposed within the fluid channel 70. For example, the capacitive sensor 74 includes a floating electrode 76 spaced apart from and opposing sensing electrodes 78 and 80 within the fluid channel 70 to provide a volumetric sensing area (e.g., corresponding to the area of overlap between the floating electrode and associated sensing electrodes). The capacitance of the sensor 74 is based on permittivity of material (or the absence thereof) in the chamber between electrodes 76, 78 and 80. In an example, as disclosed herein, the material in the chamber includes a volume of a blood sample and a bioactive agent, which interact to provide a permittivity that varies over a time interval. The sensing electrodes 78 and 80 in the capacitive sensor 74 can be electrically isolated from each other. The RF input signal is applied by the sensor interface 82 to the input sensing electrode 76 for excitation of the capacitive sensor 74 and the other sensing electrode 80 is coupled to provide $RF_{OUT}$ signal to the sensor interface 82 (see, e.g., FIG. 3).

As demonstrated in the example cross-sectional view of FIG. 2, the capacitive sensing structure 74 includes planar sensing electrodes 78 and 80 that are separated from a floating electrode 76 by the microfluidic channel 70 to form a capacitive sensing area with nominal air-gap capacitance, $C_0$, which is defined by the overlapping electrode area and microfluidic channel height. For example, at the excitation frequency, $\omega$, the capacitive sensing area admittance is $Y_S = \omega C_0 \varepsilon''_r + j\omega C_0 \varepsilon'_r$, when the channel is loaded with an SUT having a complex dielectric permittivity of $\varepsilon_r = \varepsilon'_r - j\varepsilon''_r$. In the example of FIGS. 1, 2 and 3, the sensing structure is electrically connected to the output node, to provide an output signal $RF_{OUT}$ such as $V_{OUT} \propto V_{RF}\omega C_0(\Delta\varepsilon''_r + j\Delta\varepsilon'_r)$ when the sensor is driven by the input RF/microwave signal ($V_{RF}$) and the fluid channel 70 is loaded with an SUT having $\Delta\varepsilon_r$.

As also demonstrated in the cross sectional view of FIG. 2 (and the assembly view of FIG. 3), the microsensor 60 can be fabricated in multiple parts that are attached together to provide a resultant sensor structure. As shown in FIG. 3, for example, the microsensor 60 includes a top part 84 and a bottom part 86 that is spaced apart from the top part by an intermediate channel layer 88. The bottom part 86 includes the floating electrode 76 fabricated on a surface of the substrate layer. Electrodes 78 and 80 are disposed on a corresponding surface of its substrate layer of the top part 84.

In this example, a bioactive agent 89 is disposed on the blood-contacting surface of the floating electrode 76. As disclosed herein, the bioactive agent may be disposed on other electrodes (e.g., electrode 78 and/or 80), on all of the electrodes or on any surface or combination of surfaces exposed to blood within the fluid chamber 70. The blood sample thus interacts with the bioactive agent within the chamber and is modified according to the properties of the agent. For example, the bioactive agent may be in the form of a coating applied to the surface of the electrode that is exposed to contact blood placed within the chamber 70. In addition to or as an alternative to applying the coating to one or more electrodes in the chamber, one or more bioactive agents may be otherwise introduced and/or mixed with the blood sample that is introduced into the chamber 70. As mentioned, the bioactive agent can be adapted to promote, accelerate, or inhibit coagulation of blood, such as to affect the coagulation pathway deterministically.

As one example, the bioactive agent is a procoagulant. In another example, the bioactive agent is an anticoagulant. Examples of some bioactive agents that may be utilized, individually or in combination, include collagen, fibrinogen, inorganic polyphosphate (PolyP), chitosan, kaolin, phosphatidylserine (PS), Adenosine 5'-diphosphate (ADP), thrombin receptor-activating peptide (TRAP), aprotinin, Tissue Factor (TF) and the like.

As one example, ADP, TRAP, and collagen may be applied to the surface of one or more electrodes 76, 78, 80 (or other surfaces) within the chamber 70 to assess platelet response in whole blood. As another example, tissue factor, kaolin, and phosphatidylserine may be applied to the surface of one or more electrodes 76, 78, 80 (or other surfaces) within the chamber 70 to assess coagulation factor response. In yet another example, aprotinin may be applied to the surface of one or more electrodes 76, 78, 80 (or other surfaces) within the chamber 70 to assess hyperfibrinolytic state compared to a response on tissue factor-coated electrodes. Thus, as the blood sample interacts with the bioactive agent within the chamber, the effect of such blood-agent interaction on hemostasis can be monitored by measuring the dielectric permittivity of the blood sample over a time interval. As disclosed herein, the dielectric permittivity of the modified blood sample can be computed based on the RF output signal that is measured over time. The measured dielectric permittivity can be further analyzed (e.g., by a computing device) to provide an assessment of a hemostatic dysfunction of the blood sample.

By way of example, the assessment of hemostatic properties may include identifying one or more mechanisms contributing to the hemostatic dysfunction, such as corresponding to dysfunction in a part of the blood coagulation pathway. The analysis further may determine a diagnosis for a hemostatic disorder. In some examples, the determined diagnosis and/or other hemostatic assessment is further used (e.g., by the computing device) to generate an output, such as a readout parameter, specifying a recommended therapy to apply based on the dielectric permittivity values. In certain applications (e.g., trauma situations), the recommended therapy includes administering intravenously a solution containing platelets, saline, recombinant fibrinogen, tranexamic acid (TXA), prothrombin complex concentrate (PCC), recombinant coagulation factors, plasma, or whole blood (WB), which therapy will depend on the readout parameter of the system. In an example, the output can indicate the specific type of solution to administer as the recommended therapy based on analysis of the dielectric permittivity values and according to defined standard of care.

As a further example, the sensing electrodes 78 and 80 each extend from opposite side edges of the substrate beyond a central longitudinal axis of the microsensor 60 to terminate in respective ends near a central portion of the substrate. The middle layer part 88 has a thickness that determines a volume of the channel 70 formed therein. The top part 84 can include the inlet/outlet ports 72 to provide fluid communication for accessing the volume defined by the channel 70. For example, the channel 70 in part 88 and associated ports 72 can be fabricated by micromachining (e.g., laser micromachining) or by other types of machining or etching techniques. In some examples, the surface of channel 70 further can be coated with a polymer or other material (e.g., electrically insulating film, such as poly (ethylene glycol)) to help protect against protein adsorption onto the surfaces that contact the protein solutions. The polymer can be applied via physisorption or chemisorption principles, for example.

As an example, the substrate layers for the top and bottom parts 84 and 86 can be fabricated using poly(methyl methacrylate) (PMMA). The intermediate channel substrate layer 88 can be formed of a thin film layer of double-sided-adhesive (DSA) material having a thickness that is much less than the electrode-containing substrate layers 84 and 86. As one example, each of the layers 84 and 86 may be about 1.5 mm thick, whereas the layer 88 is about 250 μm thick. Other relative thicknesses and/or adhesives can be utilized according to application requirements.

Each of the floating electrode 76 and sensing electrodes 78 and 80 can be formed by deposition of electrically conductive material deposited at a desired location (e.g., aligned with the sensing electrodes and within the channel 70) on the respective opposing surfaces of substrate layers 86 and 84. For instance, the floating electrode 76 can be an electrically conductive material (e.g., gold, copper or aluminum) deposited on the inner top surface of the cap by sputter deposition using a shadow mask and lift-off process. As an example, 100-Å/1,000-Å Cr/Au layer is evaporated on the channel surface of the substrate to form respective sensing electrodes 78 and 80. Similarly, the floating electrode 76 can be deposited on the surface of the layer 86 by evaporating a 1,000-Å Au layer and patterning with lift-off.

As shown in FIGS. 1, 2 and 3, to facilitate construction of the sensing apparatus 60, in some examples, each of the layers 84, 86 and 88 may include a plurality of alignment holes 90. Each of the layers can be connected together and held in place by inserting corresponding alignment pins (not shown) into the holes 90. In some examples, a thin film coating of a barrier material can be deposited on the surfaces of the layers 84, 86 and 88 to protect the metal and plastic surfaces from direct contact with the SUT. In this example, the bioactive agent can be disposed over the thin film on one or more electrodes. In other examples, no coating may be used to help increase sensitivity and the bioactive agent may be applied directly to one or more surfaces within the chamber, such as disclosed herein.

In some examples, microfluidic inlet/outlet holes 72 in the layer 84 can be configured with a diameter to fit a standard micropipette tip or a syringe containing a volume of the sample. As one example, the microfluidic channel 70 has a total sample volume of less than about 10 μL (e.g., about 5-9 μL) and a volume of less than about 1 μL (e.g., about 0.8 μL or less) in the sensing area over the floating electrode 76. Other volumes for the channel and sensing area can be implemented according to application requirements. The micro sensor 60 can be assembled by attaching the substrate layers 84 and 86 together using the intermediate layer 88 interposed therebetween.

As shown in the example of FIG. 3, electrical connections to the sensing electrodes 78 and 80 may be made by respective connector pins 62 (or other terminals) extending through contact openings 94 in opposed side edges of the substrate layer 86 to electrically connect to contact pads 95. The pins 62 can be electrically connected to the sensor interface system (e.g., to transmitter 22 and receiver 24 of interface 14) through electrical traces 96 on the circuit board layer 98. That is, connectors (e.g., pins) 62 are mounted on the circuit board and are electrically coupled through traces 96 to the sensor interface 82 (e.g., sensor interface 214 of monitoring system 200). After the measurement process is complete, the sensor 60 may be disconnected from the circuit board and discarded in an appropriate manner.

In the example of FIGS. 1, 2 and 3, the sensor 60 is demonstrated along with its terminals that can be electrically connected to interface electronics on the printed-circuit board (PCB) 98. In some examples, the connection between the microsensor 60 and interface system 214 (FIG. 6) can be configured as a plug-and-play-type modular connection between the sensor contact pads and PCB input/output (e.g., using spring-loaded contact pins 62 to provide an electrical connection). The connection method facilitates DS measurements with potentially hazardous or contaminating solutions, since the low-cost sensor (e.g., a cartridge or modular sensing apparatus 60) can be replaced after a measurement has been made for a given SUT without contaminating the entire instrument. That is, in some examples, each microsensor 60 is intended for single use, which can be discarded and replaced by another microsensor after each use, while the interface system 214 and associated electronics can be re-used. In other examples, a given sensor 60 can be repeatedly reused for a plurality of measurements with the same or different SUTs.

Figure 4:
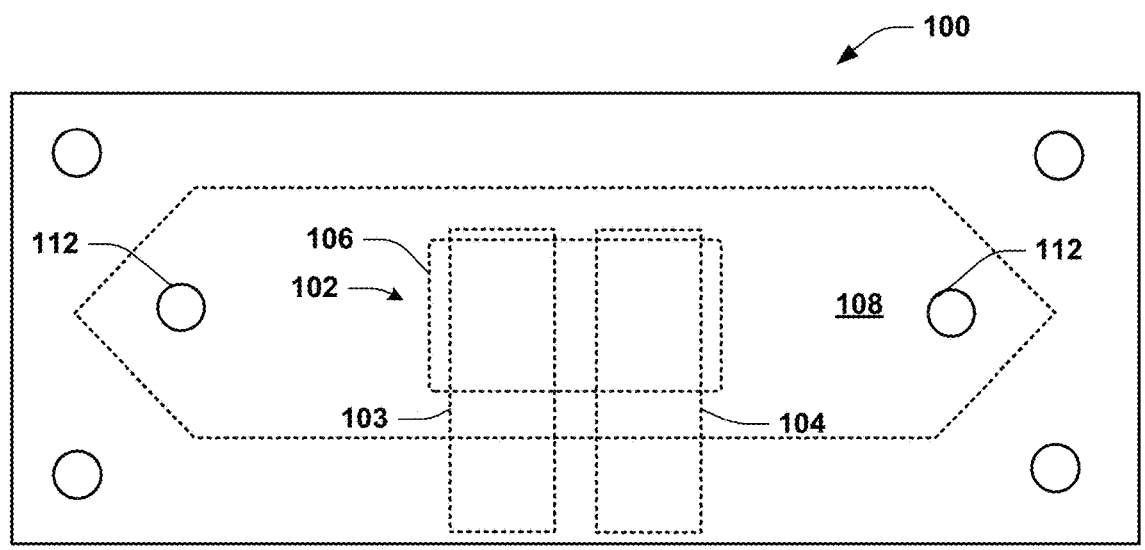
FIG. 4 depicts an example of another dielectric microsensor.
Figure 5:
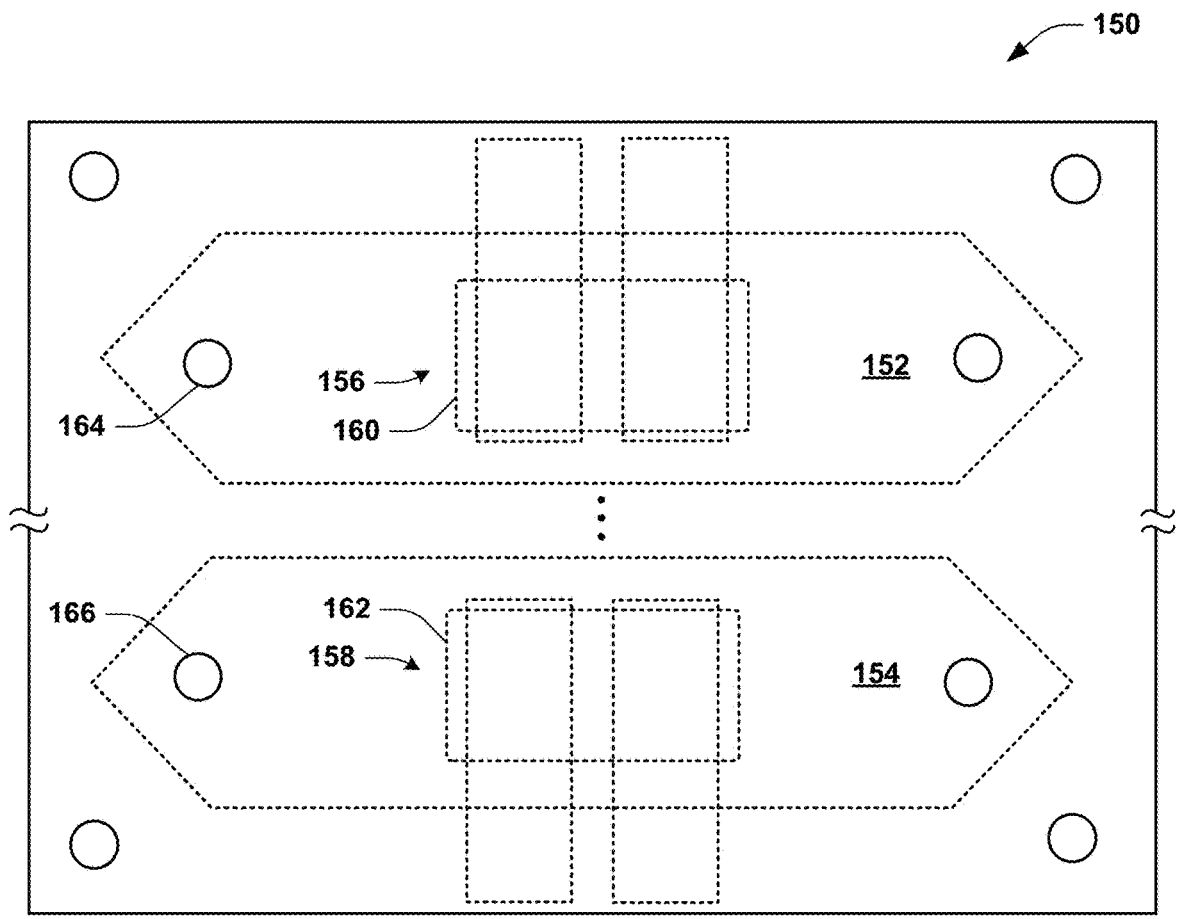
FIG. 5 depicts an example of another dielectric microsensor with multiple sensing structures.

FIGS. 4 and 5 depict examples of other dielectric sensor apparatuses 100 and 150 that may be implemented and used for assessing hemostatic properties of blood. In the example of FIG. 4, the sensor apparatus 100 includes a three-dimensional, parallel-plate, capacitive sensing structure 102. The capacitive sensing structure 102 includes two planar sensing electrodes 103 and 104 that are spaced apart and are separated from a floating electrode 106 according to a height of a microfluidic chamber (e.g., chamber 70, 108) to form a 3D capacitive sensing area disposed within the microfluidic channel. The capacitive sensing structure 102 is disposed within a substrate material 110. The sensing apparatus 100 includes ports 112 (e.g., inlet and outlet holes) through which a volume of fluid sample (e.g., blood) can be introduced into a respective chamber 108.

A cross sectional view of the sensing apparatus 100 would be similar to that shown in the example of FIG. 2, and reference may be made back to FIG. 3 and its discussion for an understanding of how different portions are constructed and attached together resulting in the sensing apparatus 100. That is, a similar overall fabrication and assembly procedure that can be employed to produce the sensing apparatus 100 of FIG. 2 as well as the sensor apparatuses 100 of FIG. 4 and 150 of FIG. 5. In the example of FIG. 4, the sensing electrodes are formed of parallel electrodes that extend from a common side edge of a corresponding substrate layer (instead of from opposed side edges as in the example of FIG. 2). In an example, the sensing apparatus may include a known bioactive agent within the chamber to interact with the blood sample. In some examples, a plurality of different bioactive agents may be disposed for interacting with blood in chambers of different sensing apparatuses to elicit different corresponding RF output responses that provide respective dielectric values that vary according to the blood-agent interactions. The different responses may be analyzed relative to each other and expected results (e.g., stored in memory) to generate an assessment of hemostatic properties (e.g., dysfunction) for the blood sample based on the dielectric permittivity values for each of the samples.

FIG. 5 depicts an example of a multi-chamber sensing apparatus 150. The apparatus includes a plurality (e.g. two or more) of microfluidic chambers 152 and 154. Each of the chambers includes a respective capacitive sensing structure 156 and 158. While two chambers and associated sensing structures are illustrated in FIG. 5, there can be more than two in other examples.

For example, each capacitive sensing structure 156 and 158 includes an arrangement of plurality of conductive plates spaced apart, such as disclosed herein. In this multi-chamber example, at least one of the plurality of microfluidic chambers includes a predetermined bioactive agent to interact deterministically with a sample of blood within the chamber between the electrodes, such as including one or more agents disclosed herein. For example, the bioactive agent is disposed on the surface of one or more conductive elements (e.g., element 158, 160) of each capacitive sensing structure or another surface in the respective microfluidic chamber. In some examples, the chamber and capacitive sensing structure of at least one of the plurality of microfluidic chambers does not include any bioactive agent to contact the blood sample received therein. Thus, the blood sample in such sensing structure 156 does not interact with any bioactive agent (due to the absence of bioactive agents from such chamber) while the sample in one or more other sensing structures 158 interact with respective bioactive agents adapted to alter hemostatic properties of blood in a deterministic manner. Thus, DS measurements, such as disclosed herein for the blood samples in different chambers, provide a comparative analysis of hemostatic properties of the blood. The blood can be introduced into each chamber 152 and 154 via one or more fluid ports 164 and 166. In some examples, healthy blood will react in an expected deterministic way, whereas blood having a disorder will not respond in the expected deterministic way.

By way of example, each of the sensing structures 156, 158 can be interrogated by the same RF input signal over a time interval and resulting RF output signals can be measured and processed by hardware and/or software, such as disclosed herein. For example, associated circuitry (e.g., including a computing device) is programmed to determine the assessment of hemostatic dysfunction based on the dielectric permittivity values computed for the blood sample introduced into two or more of the microfluidic channels. As a further example, the computing device is programmed to calculate a difference (or other comparative or correlative functions) between the dielectric permittivity values computed for samples in each of the microfluidic chamber 152, 154 and determine the assessment of hemostatic properties for the blood sample based on the difference (or other comparative or correlative functions) in permittivity calculated among the samples.

Figure 6:
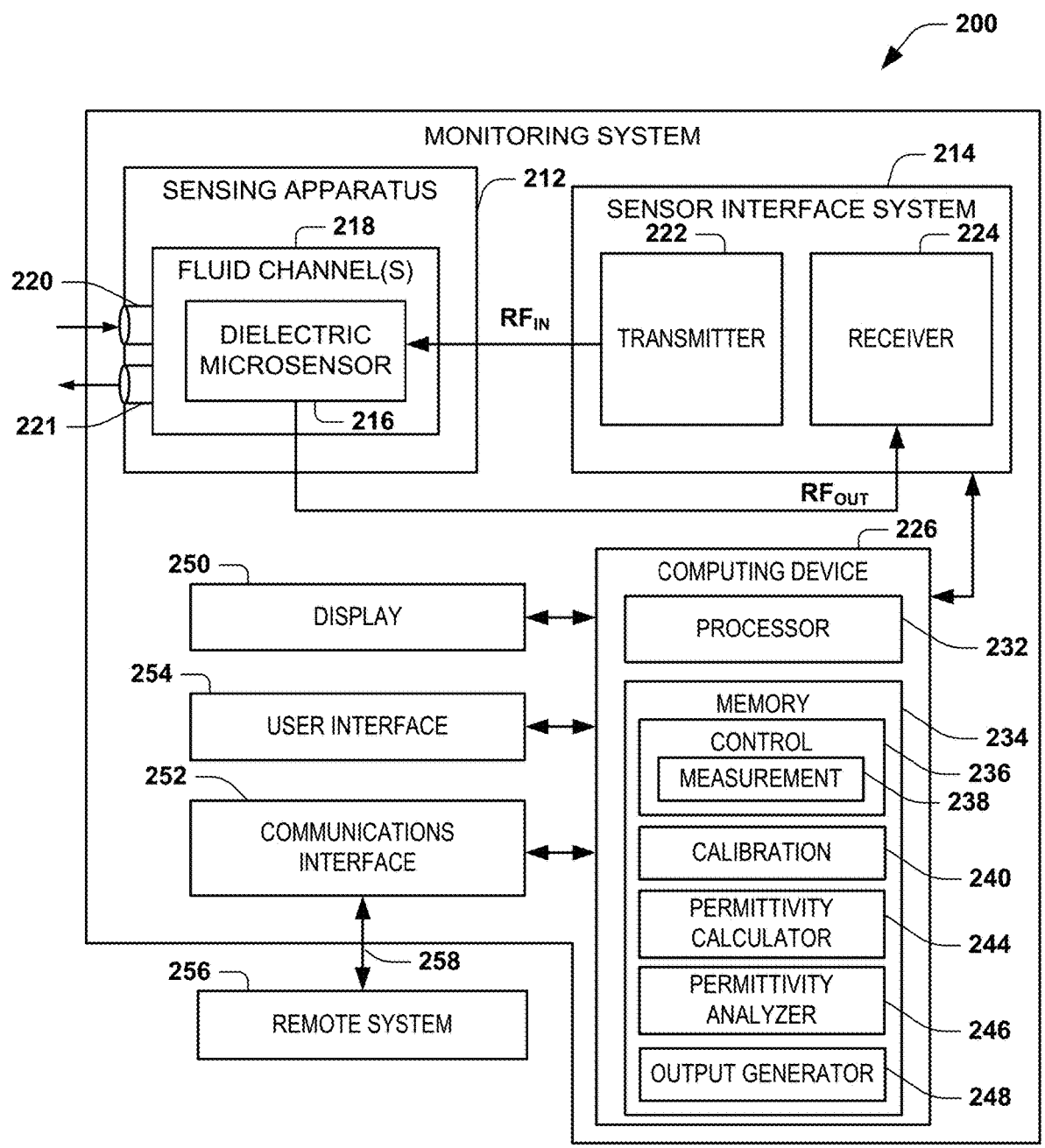
FIG. 6 depicts an example of a sample monitoring apparatus.

FIG. 6 depicts an example of a system 200 to determine properties of a sample under test (SUT) based on dielectric permittivity measurements of the sample. The system 200 can include one or more sensing apparatuses 212 (e.g., corresponding to sensor 60, 100 or 150) and a sensor interface system 214 (e.g., corresponding to interface 82). The sensor interface system 214 can drive each (one or more) dielectric microsensor 216 with an RF input signal ($RF_{IN}$). For example, each dielectric microsensor 216 is a dielectric spectroscopy (DS) microsensor that includes circuitry (e.g., an arrangement of electrodes) residing in a fluid channel 218 to measure impedance of the microsensor. The dielectric microsensor 216 is configured to have a dielectric permittivity that corresponds to its measured impedance and which depends on the SUT that is placed in the fluid channel 218 and in the gap between sensing and floating electrodes. For example, the SUT can be provided (e.g., from a source of fluid, such as a micropipette or syringe) into the fluid channel 218 via one or more fluid ports 220. In some examples, the fluid SUT can be substantially still within the channel 218 or, in other examples it can be flowing through the channel during measurements. The fluid channel 218 can be a microfluidic chamber having a volume that is less than about 10 μL, for example.

As disclosed herein, one or more samples may include blood in combination with a bioactive agent. The bioactive agent may be disposed in the channel 218 prior to introducing the blood sample or the agent may be introduced into the channel concurrently with the blood sample. A non-modified blood sample may be introduced for additional measurement in another fluid channel 218, such as for a multi-channel sensing apparatus. In this way, dielectric properties of blood interacting with one or more different bioactive agents may be compared or correlated with respect to each other and, in some examples, with respect to a non-modified blood sample. This comparative information can be leveraged to ascertain a deviation from a healthy blood coagulation profile.

As an example, the dielectric microsensor 216 can include electrodes distributed in the channel 218 in an opposing and spaced apart relationship as to provide a capacitive sensing area between opposing surfaces of the spaced apart electrodes. For instance, a floating electrode can be fixed with respect to a given surface of the fluid channel in a spaced apart opposing relationship from a pair of sensing electrodes fixed with respect to another surface of the channel. The pair of sensing electrodes thus can be substantially coplanar along a given surface of the fluid channel 218 that opposes and is parallel to the surface of the floating electrode. Other forms of capacitive sensing structures may be utilized to implement the one or more dielectric microsensors 216 in other examples.

The sensor interface system 214 includes a transmitter 222 and a receiver 224 (e.g., may be integrated into a transceiver). The transmitter 222 can be configured to provide the RF input signal at a desired excitation frequency. The excitation frequency, for example, can be in the microwave range. For instance, the transmitter 222 can provide the RF input signal that sweeps through a range of frequencies, such as from about 1 KHz to about 100 GHz (e.g., from about 1 KHz to about 100 MHz). The frequency range may be a continuous range through which the excitation is swept. In other examples, the transmitter 222 can provide $RF_{IN}$ at a plurality of different discrete excitation frequencies, which can be set according to the SUT and application requirements. As one example, for monitoring blood SUT's, the transmitter 222 can provide $RF_{IN}$ to include at least frequencies at about 1 MHz and also at about 100 MHz. The excitation frequency(ies) can be set in response to a programming input signal (e.g., via user interface 254 of the apparatus or sent from a remote system 256), such as to adjust the frequency according to application requirements to maximize sensitivity of the sensor. The frequency range for the excitation signal can be continuous across the range or be provided in two or more discrete frequency bands, which can be user programmable (e.g., in response to a user input). For example, one of the sensing electrodes of each dielectric microsensor 216 can be configured to receive the RF input signal ($RF_{IN}$) as an excitation signal from the transmitter 222 of the sensor interface system 214 and the other sensing electrode can provide a corresponding RF output signal ($RF_{OUT}$) to the receiver 224 of the sensor interface system.

The receiver 224 is configured to provide an output signal (OUT) representing measured sensor transmission characteristics based on the RF output signal from each dielectric microsensor 216 implemented in the sensing apparatus 212. The output signal can be an analog signal or be converted to a digital signal (e.g., via an analog-to-digital converter). The receiver 224 can include circuitry configured to process the RF output signal, such as by amplifying (e.g., variable gain) and filtering the RF output signal to ascertain complex signal components of $RF_{OUT}$, which filtering can be configured according to the frequency or frequency range of the excitation signal $RF_{IN}$. The RF output signal can be a complex signal corresponding to voltage transmission measurements through the dielectric microsensor 216, which varies as a function of the complex impedance or admittance as seen at an output node thereof (e.g., demonstrated at $RF_{OUT}$ in various figures herein). That is, $RF_{OUT}$ can have a predetermined relationship with respect to a change in dielectric permittivity caused by the blood sample within the channel 218 over time. In an example, the blood sample interacts with a bioactive agent in the fluid channel 218. The bioactive agent may alter hemostatic properties (e.g., modify clotting kinetics and/or coagulation pathway) of the blood sample in a deterministic manner, which causes a corresponding change in dielectric permittivity of the blood sample within the fluid channel 218. This change in dielectric permittivity is determinable from monitoring the RF output signal over time.

The transmitter 222 and receiver 224 can be implemented in an integrated circuit chip (e.g., system on chip) or they could be implemented as separate components configured to perform the functions disclosed herein. While the transmitter 222 and receiver 224 are demonstrated in FIG. 6 as co-residing in the interface system 214 (e.g., in a single IC chip), in other examples, the transmitter and receiver could be implemented as independent separate circuits.

In the example of FIG. 6, the sensor system 200 also includes a computing device 226. The computing device 226 can include a processor (e.g., having one or more processor cores) 232 and memory 234. The memory 234 can store instructions and data, and the processor 232 can access the memory to execute the instructions based on the stored data to perform functions and methods disclosed herein.

For example, the memory 234 stores control functions 236 which, when executed by the processor 232, control operation of the sensor interface system 214. For example, the DS control 236 can selectively control the range of frequencies (e.g., frequency bands) of the RF signal ($RF_{IN}$) applied by the transmitter 222 to each respective dielectric microsensor 216. The control 236 also includes instructions executable by processor 232 to perform measurement functions 238 based on the output signal ($RF_{OUT}$) that is received at the receiver 224 from each respective dielectric microsensor 216 in response to $RF_{IN}$.

As an example, the measurement function 238 is configured to measure complex impedance based upon amplitude and phase provided in the output signal $RF_{OUT}$. For instance, the measurement function 238 cooperates with the sensor interface system 214 to operate as an impedance analyzer. In this way, the measurement function 238 measures the complex impedance, corresponding to the capacitance of the dielectric microsensor 216 that varies based on the dielectric permittivity of the blood sample disposed within the fluid channel 218 and in response to the input excitation signal $RF_{IN}$. As mentioned, the transmitter 222 can provide $RF_{IN}$ as an excitation signal at one or more discrete frequencies or sweep across one or more predefined frequency bands. The measurement function 238 thus stores impedance (e.g., capacitance) measurement values and associated timestamps (e.g., a time index) as time-based impedance data in the memory 234 based on the RF output signal from the dielectric microsensor 216. Additional information (e.g., metadata) may also be stored in the impedance data, such as to specify the input signal frequency, the particular type of bioactive agent, time and date, an identity of the SUT and/or patient, temperature and/or other parameters associated with each SUT.

By way of further example, during the first portion of a test phase, control 236 can control the transmitter 222 to provide the RF input signal ($RF_{IN}$) within a first range of frequencies (e.g., a low frequency range). During one or more subsequent or other different phases of the sensing process, the control 236 can command the transmitter 222 to provide the RF input signal $RF_{IN}$ for one or more different ranges of frequencies for exciting the sensor and the associated SUT disposed in the fluid channel 218. For example, different frequencies may be used to extract different properties of the SUT, which may vary over a measurement time interval. The receiver 224 thus can receive and sample corresponding output signals $RF_{OUT}$ associated with each phase of the sensing process. The control 236 can also control the receiver 224 to provide the RF output data as a DC output voltage in the I-mode and another DC output voltage in the Q-mode. While the control and measurement functions 236 and 238, respectively, have been described as being part of the computing device 226, in other examples, the measurement and control functions could be distributed between the sensor interface system 214 and the computing device 226 or be implemented separately from the computing device (e.g., as part of the sensor interface or as a separate control system).

The computing device 226 further can include data processing methods and/or functions 236, 244 and 246 for computing permittivity based on the output data provided by the measurement function 238 for a given measurement interval. For example, the computing device 226 further can process the received RF output signals ($RF_{OUT}$) from a given dielectric microsensor (or from multiple microsensors) 216 and provide output data that includes the impedance measurements as well as dielectric permittivity data and other information derived from the measurements to represent complex dielectric permittivity, raw data corresponding to the measured RF output signals as well as other information derived therefrom. A corresponding data set can be stored in the memory 234 for each of the dielectric microsensors 216 according to the respective input and output ($RF_{IN}$ and $RF_{OUT}$) signals.

As a further example, the computing device 226 includes a calibration function 240 programmed to determine a calibration permittivity for a given dielectric microsensor 216. For example, the control function 236 can control transmitter to provide $RF_{IN}$ that is at or includes a predetermined excitation frequency (or frequency band) in which two or more substantially different SUTs are known to have little or no difference in permittivity. Thus, different types of samples may utilize different excitation frequencies for calibration as well as for testing depending on the samples. For the example of a blood SUT, the calibration input frequency can be about 100 MHz. In this way, the measured impedance (e.g., capacitance) corresponds to the capacitance of water, and the resulting permittivity derived (e.g., by permittivity calculator 244) from $RF_{OUT}$ in response to $RF_{IN}$ at the calibration frequency provides a measure of water permittivity for the dielectric microsensor 216. That is, the calibration capacitance and permittivity represent the capacitance and permittivity of the dielectric microsensor 216 with an SUT in the channel 218 with a known permittivity value (e.g., water has a known permittivity of approximately 80 at 100 MHz). This calibration measurement of impedance (e.g., by measurement function 238) and determination of the calibration permittivity (e.g., by permittivity calculator 244) may be implemented as part of the normal sensing process while an SUT is within the fluid channel 218, such as described above, so long as the excitation is provided at an appropriate calibration frequency.

By way of further example, if the sensor apparatus 212 is being used to measure the permittivity of blood, at 100 MHz, the permittivity of blood is close to that of water, (e.g., $\varepsilon_{r,blood}(@100\ MHz) \cong \varepsilon_{r,water}(@100\ MHz) \cong 80$). This relationship and calibration frequency thus may be used for water-based substances other than blood. In particular, this relationship can be used to implement a simplified calibration procedure for non-modified blood (e.g., blood not mixed with a bioactive agent) that can be implemented while the blood SUT remains in the sensing apparatus. Other relationships and different calibration frequencies may be determined and used for other types of SUTs in a like procedure.

In the example to determine the permittivity of blood at 1 MHz, including non-modified blood and blood interacting with a bioactive agent, the following procedure may be used. After the sensing apparatus 212 is attached to the system 200, blood may be inserted into the fluidic chamber of the dielectric microsensor 216 (e.g., using a micropipette). The admittance for blood (i.e., $Y_{s,blood}$) is measured over multiple frequencies (e.g., sweep 1 kHz to 100 MHz, or at 1 MHz and 100 MHz), such as disclosed herein.

The nominal capacitance for the sensor in the absence of an SUT (i.e., air-gap capacitance or $C_0$) is calculated, such as follows:

$$C_0 = \frac{Y_{s,blood}(@100 \text{ MHz})}{j \times \omega \times \varepsilon_{r,blood}(@100 \text{ MHz})},$$

where $\varepsilon_{r,blood}(@100 \text{ MHz})$ is taken as $\varepsilon_{r,blood}(@100 \text{ MHz}) \approx \varepsilon_{r,water}(@100 \text{ MHz}) \approx 80$.

The permittivity calculator 244 then computes the permittivity of blood at the frequency of interest (i.e. $\varepsilon_{r,blood(@1 \text{ MHz})}$) such as follows:

$$\varepsilon_{r,blood}(@1 \text{ MHz}) = \frac{Y_{s,blood}(@1 \text{ MHz})}{j \times \omega \times C_0}$$

where $C_0$ was calculated above based on the measured admittance of blood at the calibration frequency (e.g., 100 MHz).

Alternatively, the calibration measurement can be performed as a separate process for each SUT, such as before any SUT is placed in the fluid channel 218. The calibration function 240 stores the calibration permittivity value (e.g., corresponding to the air gap permittivity or capacitance) in the memory 234. In some types of sensing, such as for $T_{PEAK}$, calibration function 240 may be omitted since the time to peak for a given type of material is not affected by calibrating or not calibrating permittivity of the sensor.

The permittivity calculator 244 is also executed by the processor 232 to determine dielectric permittivity of the SUT. This may include for determining the calibration permittivity as mentioned above, as well as more generally during sensing. The permittivity calculator 244 thus determines the permittivity for the dielectric microsensor 216 and the SUT over a corresponding measurement time interval. This interval can range from the time in which the control 236 activates the sensor interface 214 to provide the RF input signal until a subsequent time in which the control 236 deactivates the sensor interface 214 when sensing is complete. The measurement interval may be a fixed time or it can be controlled and terminated based on monitoring the measured capacitance or determined permittivity.

As an example, the permittivity calculator 244 can determine a relative permittivity of the SUT based on a measured impedance at one or more measurement frequencies (e.g., one or more frequency bands) and based on the calibration permittivity (e.g., determined by calibration function 240). For example, the permittivity calculator 244 can compute the permittivity at a given time index and input frequency by dividing the measured impedance value (e.g., capacitance) by the calibration capacitance value (e.g., air gap capacitance) to provide a relative permittivity value for the SUT at the given time index. Additionally, in some examples, the permittivity values over the measurement interval may be normalized with respect to the permittivity at the first measurement point, peak permittivity or another value. The normalized, relative permittivity value can be computed for each of the plurality of measurement data points over a range of time indices that define the measurement time interval. Each permittivity value can be stored as permittivity data in the memory 234 for further processing and analysis. As mentioned, in some measurements (e.g., time-to-peak), calibration may be omitted and the permittivity calculator 244 can determine a permittivity of the SUT in the absence of the calibration permittivity and, in some cases, without normalization.

The processor 232 can also execute code to implement a permittivity analyzer 246 that is programmed to determine one or more permittivity parameters based upon the dielectric permittivity values computed by the permittivity calculator 244 for each respective SUT. The permittivity analyzer 246 can determine parameters for one or more different portions of the measurement time interval, including up to the entire interval. As one example, the permittivity analyzer 246 analyzes the stored dielectric permittivity values over a portion of the measurement time interval to determine a time that it takes to reach a peak dielectric permittivity value ($T_{PEAK}$). For instance, the permittivity analyzer 246 employs a peak detector function to ascertain the peak permittivity value, and the time interval (e.g., an elapsed time) to reach the peak dielectric permittivity thus can be stored in memory as $T_{PEAK}$ for the SUT. This time value $T_{PEAK}$ may be the time index associated with when the associated impedance measurement was made or it may be determined as the difference between the start time and the time when the measurement occurred to provide $T_{PEAK}$. For example, the $T_{PEAK}$ value for a given blood SUT thus can provide an indication of an anticoagulation property of the SUT. In some examples, the $T_{PEAK}$ value for the given blood SUT may further describe its interaction with a bioactive agent within the dielectric microsensor 216. The $T_{PEAK}$ value can be stored in the memory 234 for each SUT.

As another example, the permittivity analyzer 246 can be programmed to analyze the stored dielectric permittivity values to determine a difference between the peak dielectric permittivity value (at $T_{PEAK}$) and a plateau permittivity value for each SUT, which difference is referred to as $\Delta\varepsilon_{r,max}$. The plateau permittivity value can represent a permittivity value that remains substantially constant over time, such as at a tail end portion of the measurement time interval. As used herein, the term substantially constant is intended to refer to a sufficiently small rate of change from a given value over time (e.g., about ±5% or less). The permittivity analyzer 246 can determine the plateau permittivity value, for example, by determining that the time derivative of the permittivity values remains less than a predetermined value or is zero over a period of time. The difference between peak permittivity and plateau permittivity values ($\Delta\varepsilon_{r,max}$) can be used to provide an indication of additional properties associated with each respective SUT. For the example of a given blood SUT, which may be interacting with a bioactive agent, the difference between peak permittivity and plateau permittivity values can provide a quantitative measure of hemostatic properties associated with platelet function (e.g., clot stability and/or firmness).

In yet another example, the permittivity analyzer 246 can evaluate the dielectric permittivity values for the SUT over a portion of a time interval to determine the rate of change in permittivity values, such as corresponding to a slope of a portion of a curve representing the dielectric permittivity values. For instance, the permittivity analyzer 246 can determine a rising edge slope between the beginning of the measurement interval and the peak dielectric value. The permittivity analyzer 246 also may compute a falling edge slope such as between the $T_{PEAK}$ value and the plateau dielectric permittivity value. Further analysis can be made with respect to the tail portion between the peak and the plateau dielectric values to provide an indication of other properties associated with the SUT.

In some examples a plurality of different blood SUTs are introduced into different fluid channels 218 where one or more such samples are mixed with predetermined bioactive agents for interacting with the volume of the blood sample received in the respective fluid channel. In an example, the predetermined bioactive agent is disposed on a capacitive sensing structure thereof for interacting when the blood is introduced. A given sample may also include non-modified blood (e.g., without any bioactive agent). For each such SUT, the calculator 244 can compute dielectric permittivity values for each SUT based on the measured RF output signal for each of the microfluidic channels over at least one time interval (concurrent or sequential times). For example, the analyzer 246 is programmed to determine the assessment of hemostatic dysfunction based on the dielectric permittivity values computed for the blood samples in two or more of the microfluidic channels. The assessment of hemostatic dysfunction (e.g., determined by the analyzer 246) may include identifying a mechanism of the dysfunction and/or a diagnosis. In another example, the analyzer 246 is programmed to calculate a difference between the dielectric values computed over time for multiple SUTs in the microfluidic channels (e.g., each having a different bioactive agent) and determine the assessment of hemostatic dysfunction (e.g., identifying a mechanism of the dysfunction and/or a diagnosis) based on the difference in dielectric values. The analyzer 246 further can correlate the computed dielectric values or parameters derived therefrom with respect to known data (e.g., stored locally in memory 224 or remotely), which correlation can further specify a mechanism of the dysfunction and/or a diagnosis of a hemostatic disorder.

In some examples, an output generator 248 can utilize one or more computed permittivity parameters (e.g., $T_{PEAK}$ and/or $\Delta\varepsilon_{r,max}$) as a readout parameter to present associated information on a corresponding display 250 of the system 200. Additionally or alternatively, the output generator 248 can provide an output that identifies the mechanism of the dysfunction and/or diagnosis, such as determined by the permittivity analyzer 246 for each SUT. The output generator 248 can provide the output as including a visualization on the display 250, such as a graphical and/or textual representation of one or more permittivity parameters, and identify one or more mechanisms of a hemostatic dysfunction and associated coagulopathy, provide a diagnosis and/or recommend an intervention. An audio output may also be provided based on the one or more permittivity parameters.

In some cases, the display 250 may also present comparative results, which are determined by the permittivity analyzer 246 based on comparing the current results relative to a known standard or to one or more previous results for the same patient or a relevant patient population. This comparison further may be used to determine a deviation from a healthy blood coagulation profile for the patient's blood sample. When used as a patient or point-of-care apparatus, for example, the output generator 248 also generates a set of instructions that is provided as an output to the display 250, such as including a recommended therapy to administer based on the results from the permittivity analyzer 246. For example, the output may include a recommendation to administer a particular therapy, such as solution containing platelets, saline, recombinant fibrinogen, tranexamic acid (TXA), prothrombin complex concentrate (PCC), recombinant coagulation factors, plasma, or whole blood (WB), depending on the results of the permittivity analyzer 246.

As mentioned, the apparatus includes a user interface 254 to interact with the system 200. The user interface 254 may include a touch screen interface, a keypad, a keyboard, a mouse, voice interface and/or a combination thereof. As an example, a user can employ the user interface 254 to acknowledge information that is presented on the display such as before, during and after a measurement interval for a given SUT. Additionally or alternatively, a user may employ the user interface 254 to input information about the user (e.g., health and/or demographic information) and/or environment conditions. The user interface 254 can be utilized to program/configure the system 200 for one or more parts of a sensing process such as disclosed herein. For instance, the user interface 254 can be utilized to set a range of one or more frequencies, including one or more frequency bands, to utilize for the excitation signal during testing of the SUT. For example, in response to instructions entered via the user interface 254, the computing device 226 can employ control 236 to instruct the transmitter 222 (e.g., through a bus or interface) to operate accordingly, responsive to the user configuration instructions entered via the user interface 254. The instructions can be stored in memory 234 or other memory (e.g., a program register) of the transmitter 222 to control the frequency of the excitation signal and duration thereof that is applied during a test process. Additionally or alternatively, the user interface 254 can also be utilized to control the information that is presented in the display 250 as well as to perform other post processing functions (e.g., reporting functions, recording user responses to questions, etc.) and data analysis.

In some examples, the computing device 226 employs the communications interface 252 to communicate with the remote system 256 via a communication link 258. The communication link 258 can be implemented to include one or more physical connections (e.g., an electrically conductive connection or optical fiber), one or more wireless links (e.g., implemented according to an 802.11x standard, another short range wireless communication protocol or cellular data) or a network infrastructure that includes one or more physical and/or wireless communication links, such as the Internet or a private network.

The remote system 256 can include a server, a general purpose computing device (e.g., notebook computer, laptop, desktop computer, workstation, smartphone or the like) and/or it can be a special purpose system configured to interact with one or more of the system 200 via the link 258. For instance, the computing device 226 employs the communications interface 252 to send the remote system 256 permittivity-related information (e.g., any information derived therefrom) based on measurement results for one or more SUTs. As another example, the remote system 256 may send programming instructions to the apparatus to configure and/or update its operating program instructions. In an example where the remote system 256 comprises a back office system of a healthcare provider, the computing device 226 may send a copy of the raw measurement data and/or the results determined by the permittivity analyzer 246 using secure communications over the link 258 (e.g., HIPPA compliant communications). In such an example, the remote system 256 may communicate with a plurality of apparatuses. The subsequent instructions presented on the display, thus may include instructions to administer a particular therapy (e.g., a solution containing platelets, saline, recombinant fibrinogen, tranexamic acid (TXA), prothrombin complex concentrate (PCC), recombinant coagulation factors, plasma, or whole blood (WB)) based on remote evaluation of the permittivity data by a healthcare provider, who can transmit such instructions to the system 200 through the link 258 for presentation on the display 250 for the user at the point-of-care.

Figure 7:
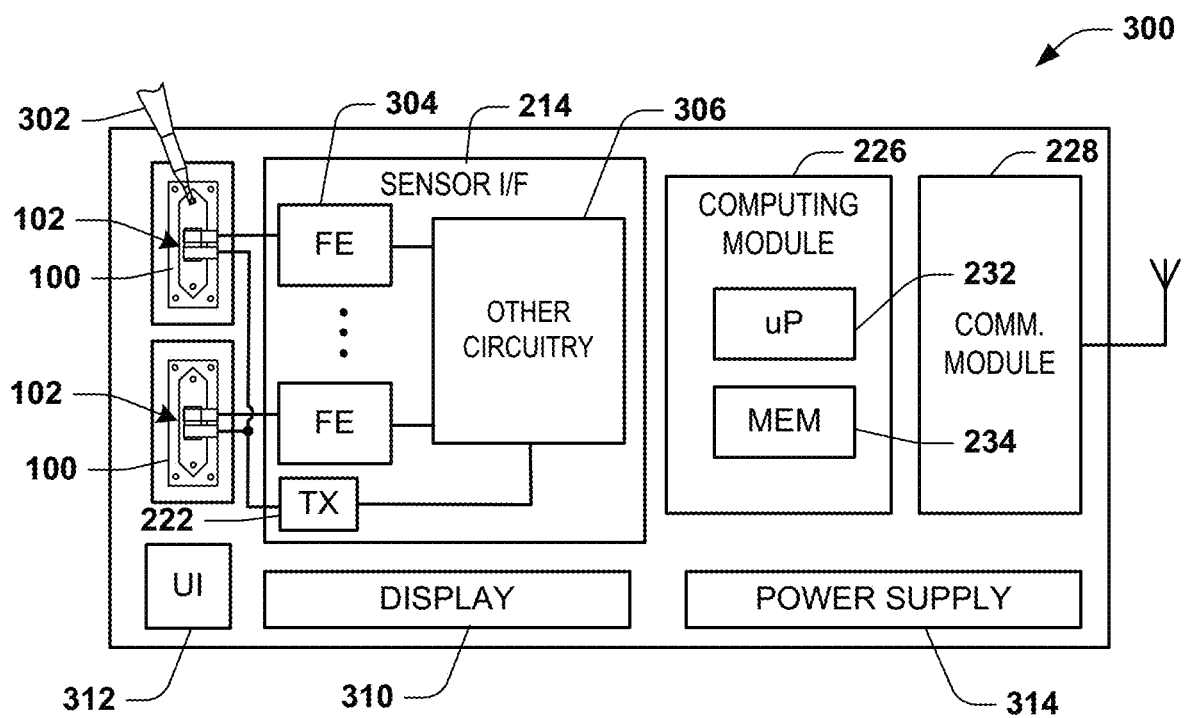
FIG. 7 depicts another example of a portable monitoring system.

As a further example, FIG. 7 depicts another example of a DS microsystem 300 that can be implemented as an integrated handheld system (e.g., the system 200), which can utilize plug-and-play sensors (e.g., as shown in FIGS. 1-5). The components of the DS system 300 can be constructed of biocompatible materials, such as including gold, glass and PMMA, commonly used in biomicrofluidic devices.

In the following description of FIG. 7, for ease of explanation and clarity, components of the system 300 are referred to using similar reference numbers that refer to components previously introduced with respect to the example of FIGS. 4 and 6. The system 300 can include one or more sensing apparatuses 100, two of which are shown in the example of FIG. 7. Also in the example of FIG. 7, each sensing apparatus 100 includes a capacitive sensing structure 102. The sensors 100 may be chips or other plug-and-play components that may be swapped into and out of the sensing system 300. For example, a user can select a set of sensors having different bioactive agents to interact with a blood sample from a particular patient, which agents enable a determination of a mechanism for a hemostatic dysfunction and/or diagnosis thereof.

Associated interface electronics 214 are coupled to inputs and outputs of each sensing apparatus 100. Thus, the sensing structure 102 and interface electronics 214 can be configured to produce a complex output that depends on (e.g., varies as a mathematical function of) the complex dielectric permittivity of the SUT (e.g., blood or other biological fluid) disposed in the respective microfluidic channel of each sensor 102 in response to an excitation signal.

As an example, a micropipette (or other device, such as a syringe or the like) 302 can be employed to inject an SUT into the microfluidic channel of the sensor 102. The sensor interface electronics 214 includes transmitter circuitry 222 to provide the excitation signal (e.g., at single frequency or frequency range of one or more frequency bands) to an input of a given sensor containing a volume of the SUT. The output of sensor 102 is coupled to respective front-end RF modules 304 (demonstrated as FE) of a receiver (e.g., receiver 224). Each front-end RF module 304 is configured to preprocess (e.g., perform down-conversion, filtering and amplification) each transmitted signal received in response to an excitation signal and provide corresponding output RF signals. The RF signals from a given one of the front-end RF module 304 can be selectively provided to other receiver circuitry 306 for further processing, such as including conversion to a digital version of the signal and provided to computing module 226. The computing module 226 can calculate permittivity for each SUT based on the system output signal to provide corresponding output permittivity values stored in memory 234 as permittivity data. The permittivity data for each sensor 102 can include real permittivity values or it may include complex permittivity values (e.g., real and imaginary permittivity) computed over the range of excitation frequencies, including different subranges provided to each sensor 102. Permittivity data can also include raw signal measurements and the input excitation frequencies. The computing module 226 can also analyze the permittivity data to determine permittivity parameters of the SUT, including a comparison and/or correlation of permittivity data for each of the sensors such as disclosed herein. The computing module 226 can provide an indication of properties of the blood based on the analysis of permittivity parameters for each SUT. One or more readout parameters describing permittivity parameters and/or hemostatic properties of the SUT (e.g., hemostatic dysfunction and associated coagulopathy) may be rendered on a display 310. The system 300 may include a user interface (UI) 312 that provides a human-machine interface to enable user interaction with the system 300, such as to review results, send results to a remote station, acknowledge instructions, reset the system or perform other human-machine interactions.

The computing module 226 can further provide the permittivity data and analysis thereof to a communication module 228. The communication module 228 can send the output data and raw measurement data to a remote system. For example, the communication module 228 can transmit the output data to a back office system (e.g., a server) that can be programmed to analyze the data and store the results and raw data in a database. The remote system can also communicate command information to the system 300 to program one or more of the system parameters (e.g., signal gain and/or frequency range) to control its operation and/or provide instructions to the user, such as disclosed herein. The system 300 of FIG. 7 can include a housing that contains the sensor interface electronics 214, computing module 226 and communication module 228 such that it can provide a portable, handheld device. The system 300 may also include an internal power supply 314, such as an internal battery and/or a power interface to connect to an external supply.

While the example system of FIG. 7 is in the context of a handheld device, in other examples, the system 300 may be implemented as a benchtop system. In this example, the system 300 may be configured to measure dielectric permittivity of a plurality of dielectric sensors 102, each having a respective SUT. Each sensor can include or share corresponding interface to provide respective measurement data to the computing module 226 for computing permittivity values for each of the respective SUTs. In this way, a laboratory or other provider can monitor a plurality of samples concurrently.

Figure 8:
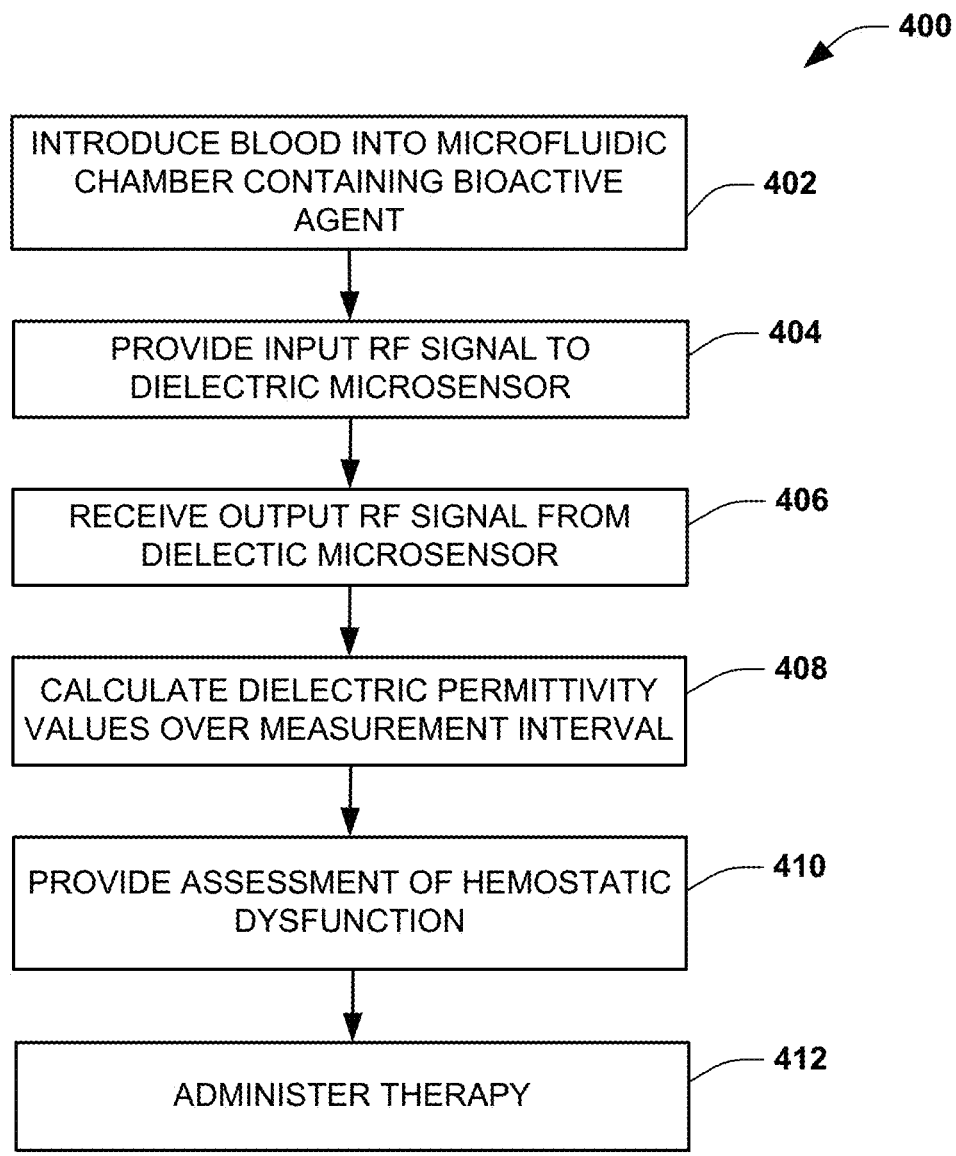
FIG. 8 is a flow diagram depicting an example of a method for using dielectric permittivity to assess hemostatic properties of a sample under test.

FIG. 8 is a flow diagram depicting an example of a method 400 to measure dielectric permittivity and determine properties of an SUT, such as a blood sample. The method may be implemented with respect to any number of one or more dielectric microsensors, such as may be implemented as any of the sensor apparatuses (e.g., sensor 60, 100, 150, 216) disclosed herein. It is to be understood that other configurations of sensor apparatuses may be used for the method 400, such as example embodiments disclosed in U.S. Patent Publication No. 2015/0346131, which is incorporated herein by reference. When more than one such microsensor is used, the method 400 may be applied to each sensor concurrently or sequentially. For example, the dielectric microsensor includes a capacitive sensing structure integrated into a microfluidic channel that includes a fluid input port to receive a sample volume of the SUT. Each sensor apparatus is attached to an interface system (e.g., interface 14) to send and receive RF signals, such as disclosed herein.

At 402, a blood SUT is introduced into the microfluidic chamber of one or more dielectric microsensors. The blood interacts with a bioactive agent within at least one microfluidic chamber over a measurement time interval. For example, the bioactive agent may be disposed within the fluidic chamber before the blood is introduced or it may be introduced with the blood. Any bioactive agent may be used including those disclosed herein. With the SUT within the dielectric microsensor, the method proceeds to 404 and an input radio frequency (RF) signal is provided to the dielectric microsensor. For example, a transmitter (e.g., transmitter 22, 222) of the interface system provides the RF input signal to an input of the microsensor. The RF input signal can include one or more frequencies, as disclosed herein.

At 406, an output RF signal is received (e.g., by a receiver 24, 224) from each dielectric microsensor in response to the applied input RF signal. The RF output signal represents a measure of impedance (e.g., capacitance) of the SUT disposed in the dielectric microsensor. As disclosed herein, measure of impedance further can vary based on interaction of the SUT with the bioactive agent. A bioactive agent may be omitted from one (or more) of the SUT in a given microsensor. The input and output signals can be communicated between the dielectric microsensor and the interface system over a measurement time interval, for example, a fixed time or a time that depends on the measurements.

At 408, dielectric permittivity values of the SUT are calculated (e.g., by permittivity calculator 244) over a measurement time interval based on the output RF signal. As disclosed herein, the permittivity may be computed as a relative permittivity and be normalized to a selected permittivity value (e.g., peak permittivity). The permittivity values may be stored in memory (e.g., memory 234).

At 410, the dielectric permittivity values of the SUT are analyzed (e.g., by permittivity analyzer 246) over at least a portion of the measurement time interval to provide an assessment of hemostatic dysfunction for the blood sample. In some examples, a volume of blood is introduced into each of a plurality of microfluidic chambers of respective sensors and dielectric permittivity values are computed for each of the respective sensors. In such an example, the assessment of hemostatic dysfunction is determined based on the dielectric permittivity values computed for at least two of the microfluidic chambers (e.g., based on a comparison of dielectric permittivity information determined for such two or more chambers). The dielectric permittivity over time for each of the samples further may be compared (e.g., by permittivity analyzer 246) to healthy blood coagulation profile data to diagnose the dysfunction and render a corresponding diagnosis. In some examples, the method 400 includes computing a difference between dielectric permittivity values determined for at least some of the microfluidic chambers and determining the assessment of hemostatic dysfunction based on the computed difference. An output can be generated at 410 to specify or recommend a therapy to administer depending on the assessment of hemostatic dysfunction and the associated coagulopathy determined based on the set of permittivity data derived from the given blood sample. A first responder or other medical professional may administer the recommended therapy to the patient at 412. In an example, the recommended therapy includes a solution containing platelets, saline, recombinant fibrinogen, tranexamic acid (TXA), prothrombin complex concentrate (PCC), recombinant coagulation factors, plasma, or whole blood (WB).

In some examples, the dielectric permittivity values may be analyzed to determine other parameters that may be indicative of cellular and/or molecular properties of the SUT, such as disclosed herein. In an example, the dielectric microsensors used in performing the method 400 are disposable, single-use devices that can be attached to the interface to enable sensing properties of the SUT and, after completing the test, removed and disposed of according to appropriate disposal procedures.

In view of the foregoing, the DS microsystem and method disclosed herein thus can provide a low-power, low-cost, portable, and field- or roadside-deployable instrument for rapidly extracting key information that characterizes the molecular and/or cellular properties of biological or other sample solutions in a broad frequency range using μL-sample volumes. In one example, the method 400 can be utilized to facilitate treatment for trauma patients at the point-of-care or point-of-injury, such as by military and civilian first responders.

Figure 9:
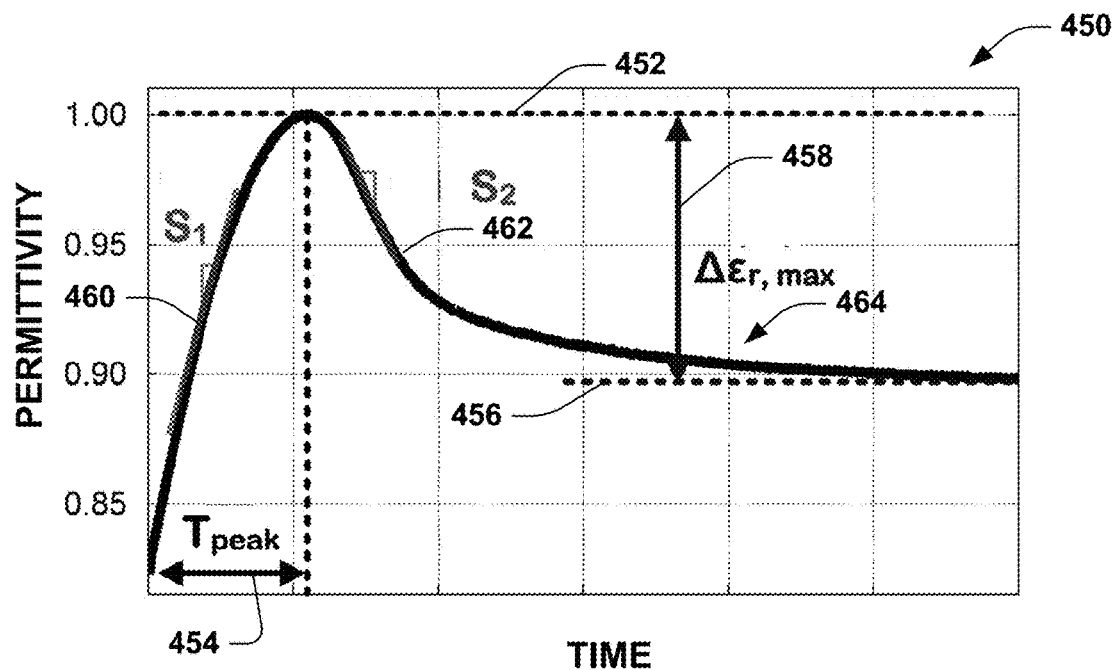
FIG. 9 is a graph depicting an example of normalized dielectric permittivity as a function of time for a blood sample.

FIG. 9 depicts an example graph 450 of normalized permittivity as a function of time demonstrating examples of permittivity parameters that can be determined (e.g., by permittivity analyzer 246) for a given SUT based on permittivity values over a measurement time interval. In the illustrated example, the measurement data and permittivity values are normalized to the peak permittivity value 452 that occurs at time $T_{PEAK}$, demonstrated at 454. In the example graph 450, the following permittivity parameters are shown: the time of peak permittivity ($T_{PEAK}$), at 454, the initial slope (S1), at 460, the slope of permittivity decline after $T_{PEAK}$ (S2), at 462, and the magnitude of the permittivity change after $T_{PEAK}$ ($\Delta\varepsilon_{r,max}$), at 458. In other examples, other permittivity parameters could be determined from analysis of the permittivity values (e.g., performed by permittivity analyzer 246), such as associated with the tail portion of the permittivity values at the end portion of the measurement interval. Each of the permittivity parameters determined from the graph 450 thus may be analyzed and compared to quantify properties of a given SUT based on the DS measurements.

For the example of a blood SUT, some properties may include cellular properties (e.g., hemostatic properties, such as platelet function or dysfunction based on $\Delta\varepsilon_{r,max}$) and/or molecular properties (e.g., coagulation factor function or dysfunction based on $T_{PEAK}$). By analyzing these and other parameters from a plurality of sensors with blood that interacts with a plurality of different bioactive agents (or no agent), systems and methods herein can determine additional information about the blood sample and patient. For example, the computing device of the measurement system can identify mechanisms of a hemostatic dysfunction, render a diagnosis and/or recommend a therapy based on the dielectric permittivity computed over time for the set of microsensors.

Figure 10:
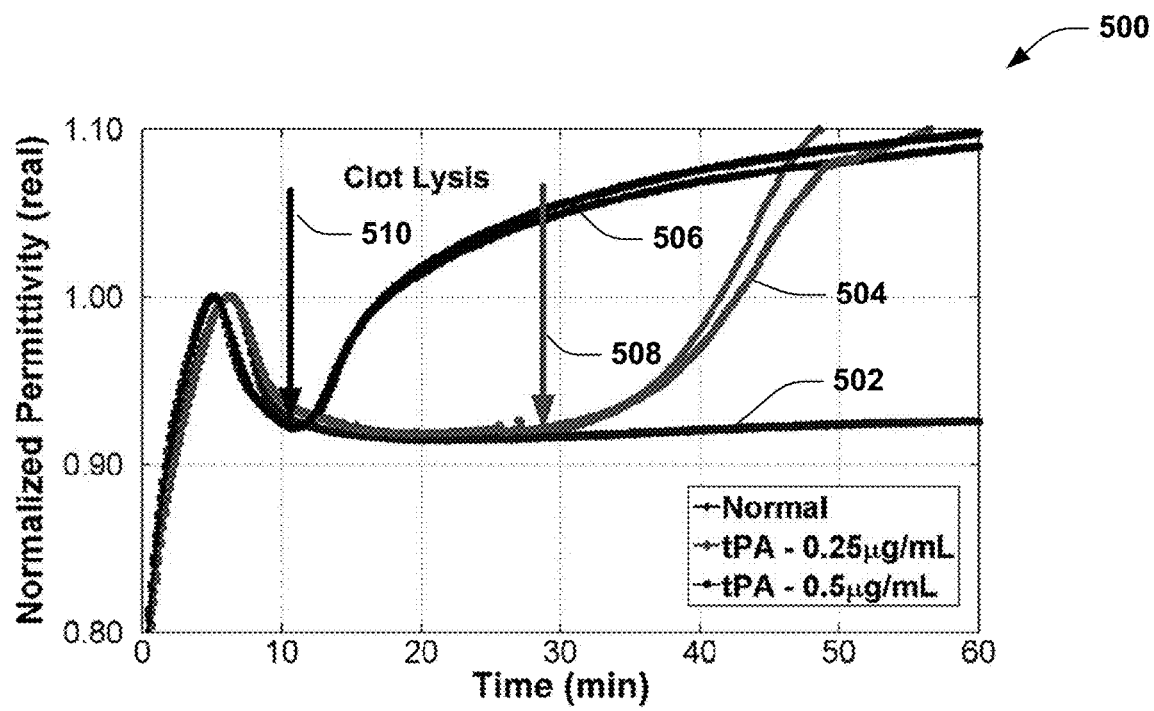
FIG. 10 is a graph depicting an example of normalized dielectric permittivity as a function of time for a blood sample undergoing clot lysis.

FIG. 10 depicts an example graph 500 of normalized real permittivity as a function of time illustrating example plots 502, 504 and 506 of normalized permittivity that can be determined (e.g., by permittivity calculator 244) over time for a given blood SUT with different levels of a bioactive agent. In particular, the graph 500 plots permittivity values over a measurement time interval to demonstrate the sensitivity of the microsensor to clot lysis (fibrinolysis) induced in a blood sample by different levels of tissue plasminogen activator (tPA). For example, the plot 502 is a normal blood sample without any tPA (i.e., in the absence of a bioactive agent). The plot 504 demonstrates normalized permittivity for blood including tPA of 0.25 μg/mL and plot 506 demonstrates normalized permittivity for blood including tPA of 0.5 μg/mL. The occurrence of clot lysis for each of plots 504 and 506 (corresponding to tPA-treated blood samples) is demonstrated by arrows at 508 and 510, respectively.

Figure 11:
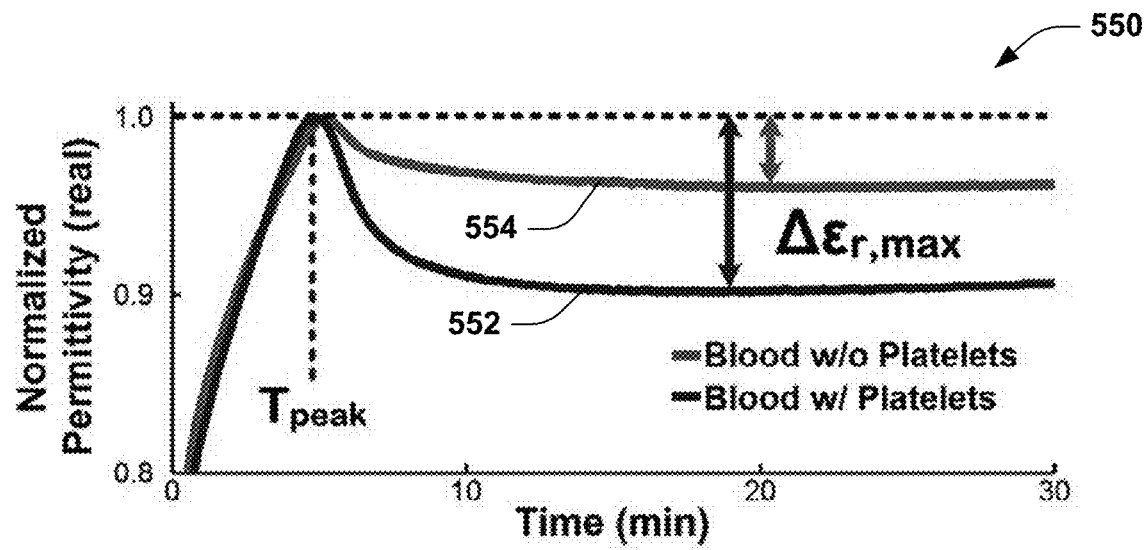
FIG. 11 is a graph depicting an example of normalized dielectric permittivity as a function of time for blood samples with and without platelets.

FIG. 11 depicts an example graph 550 of normalized real permittivity as a function of time illustrating example plots 552 and 554 of normalized permittivity that can be determined (e.g., by permittivity calculator 244) for blood samples with contrasting numbers of platelets. The permittivity may be provided on a readout of a sensor apparatus disclosed herein to demonstrate one or more permittivity parameters derived from the sensor measurement data, such as $T_{PEAK}$ and $\Delta\varepsilon_{r,max}$. The graph thus shows an example of how two blood samples undergoing coagulation with different numbers of platelets exhibit different coagulation processes represented by the different $\Delta\varepsilon_{r,max}$ parameters in the respective permittivity plots 552 and 554.

Figure 12:
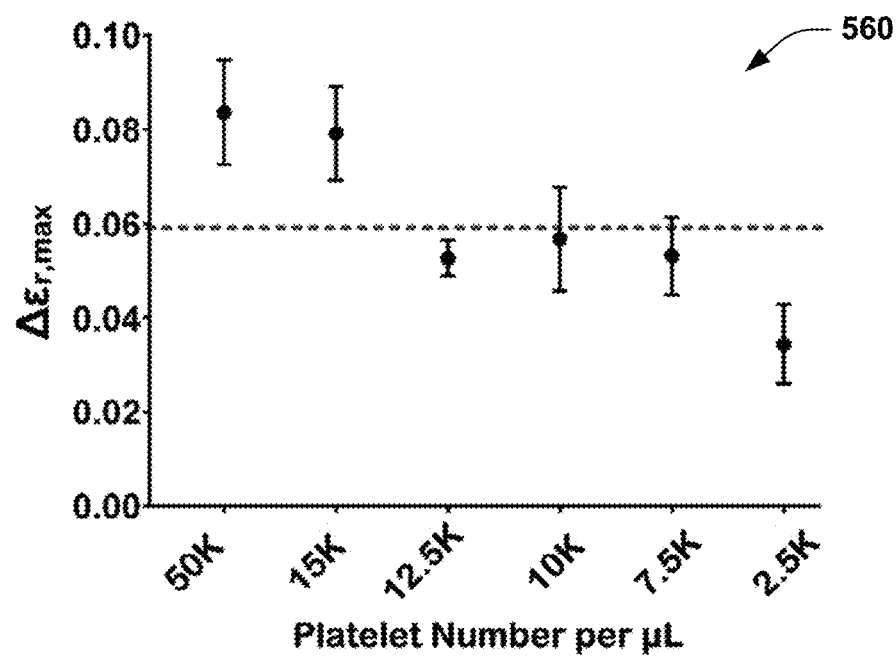
FIG. 12 is a graph of maximum change in normalized dielectric permittivity after reaching peak permittivity for blood samples having different platelet counts.

FIG. 12 is graph 560 of $\Delta\varepsilon_{r,max}$ plotted as a function of platelet count (platelet number per μL of blood). The graph thus demonstrates a decrease in the dielectric permittivity parameter $\Delta\varepsilon_{r,max}$ with decreasing platelet count in reconstituted whole blood samples undergoing coagulation, such as can be detected by microsensor and determined by the permittivity analyzer disclosed herein.

Figure 13:
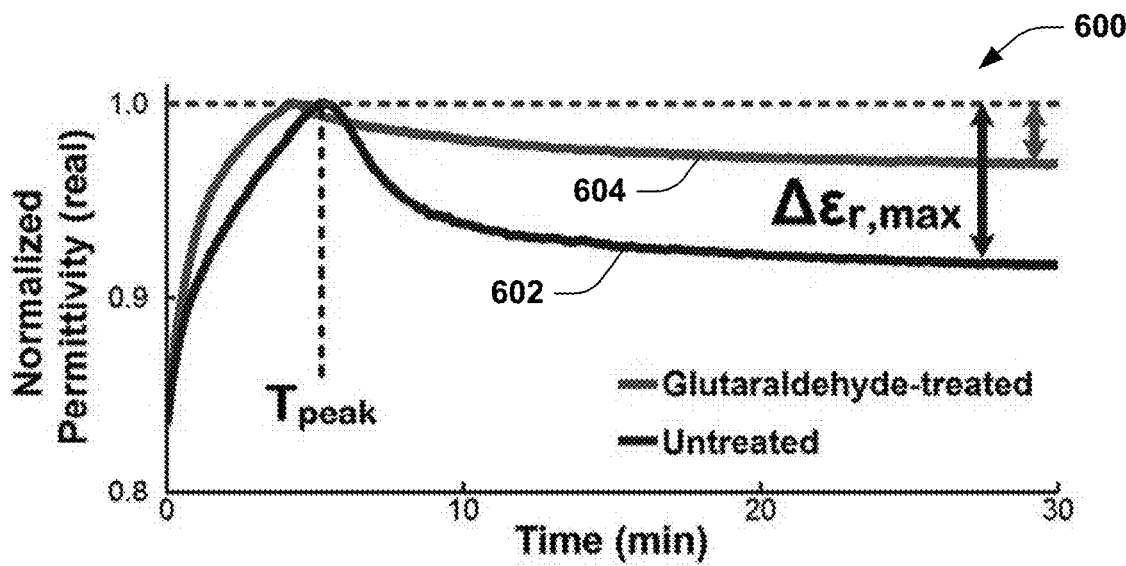
FIG. 13 is a graph depicting an example of normalized dielectric permittivity as a function of time for blood samples treated and untreated with glutaraldehyde.

FIG. 13 depicts an example graph 600 of normalized real permittivity as a function of time illustrating example plots 602 and 604 of normalized permittivity that can be determined (e.g., by permittivity calculator 244) for blood samples with contrasting levels of red blood cell (RBC) membrane elasticity. In particular, the plot 602 represents permittivity data for an untreated blood sample and the plot 604 represents permittivity for a glutaraldehyde-treated blood sample. The permittivity may be provided on a readout of a sensor device disclosed herein (e.g., device 200, 300) to demonstrate one or more permittivity parameters that can be derived from the sensor measurement data, such as $T_{PEAK}$ and $\Delta\varepsilon_{r,max}$. The graph thus shows an example of how two blood samples undergoing coagulation with different levels of RBC membrane elasticity exhibit different coagulation processes represented by the different $\Delta\varepsilon_{r,max}$ parameters in the respective permittivity plots 602 and 604.

Figure 14:
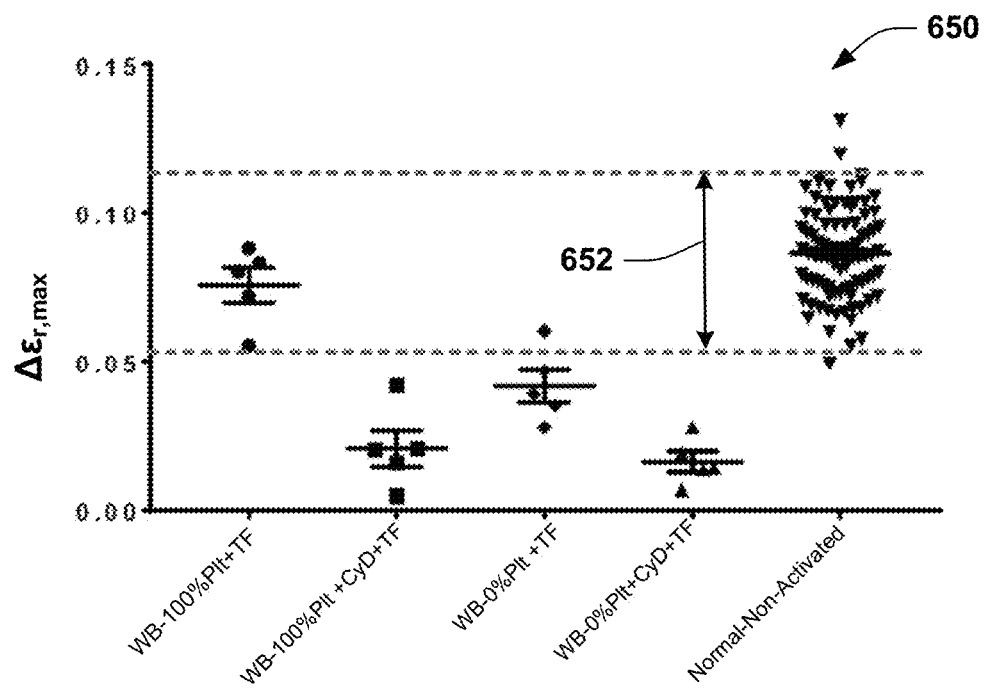
FIG. 14 is a graph of maximum change in normalized dielectric permittivity after reaching peak permittivity for blood samples having different platelet counts, with and without bioactive agents cytochalasin D (CyD) and tissue factor (TF).

FIG. 14 depicts a graph 650 of the dielectric permittivity parameter $\Delta\varepsilon_{r,max}$ plotted for blood samples having different numbers of platelets. The values of the $\Delta\varepsilon_{r,max}$ parameter for normal, non-activated blood samples fall within a range of $\Delta\varepsilon_{r,max}$, demonstrated at 652. By contrast, blood samples with reduced platelet count or otherwise impacted by bioactive agents (e.g., cytochalasin D (CyD)) exhibit $\Delta\varepsilon_{r,max}$ parameters that fall below this range 652. For example, the permittivity analyzer disclosed herein thus can determine an indication of platelet count (e.g., within normal range or outside of the normal range) and provide this information on the display to facilitate diagnosis and treatment, such as disclosed herein.

Figure 15:
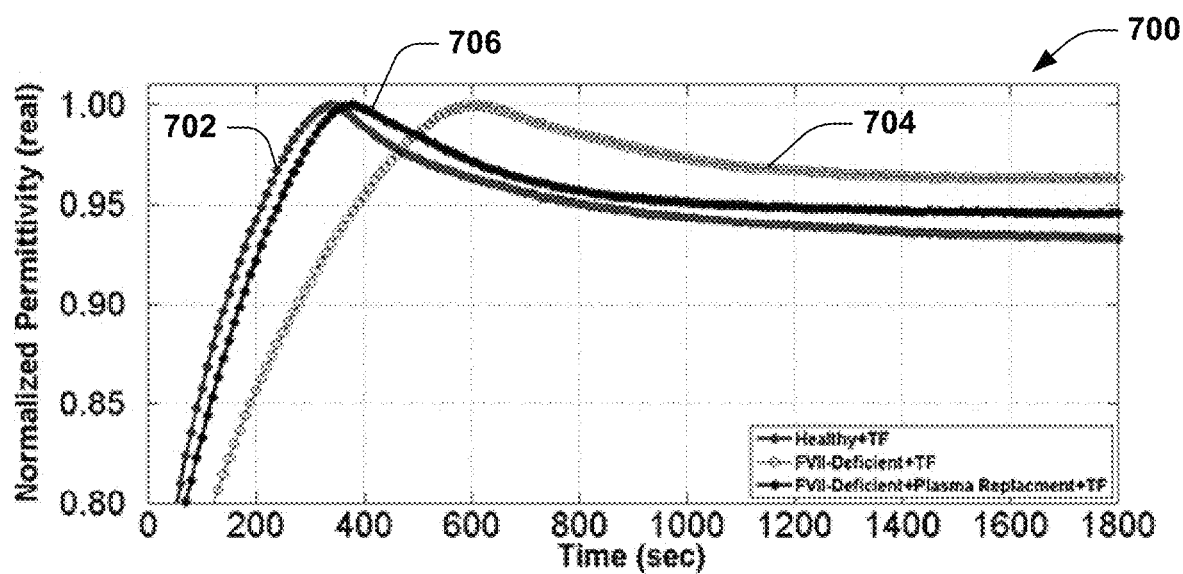
FIG. 15 is a graph depicting an example of normalized dielectric permittivity as a function of time for blood samples to which one or more bioactive agent has been added.

FIG. 15 is a graph 700 depicting an example of normalized real permittivity as a function of time for blood samples to which one or more bioactive agents have been added. In the example of FIG. 15, an amount of a coagulation factor, specifically tissue factor (TF) has been added to the blood samples. The graph shows several permittivity curves, including for a healthy sample 702, a sample with Factor VII (FVII) deficiency 704, and the same FVII-deficient sample with the addition of fresh, healthy plasma 706. As shown in the graph 700, the Factor VII-deficient sample exhibited a prolonged $T_{peak}$ compared to the healthy sample, illustrating that the sensor can detect the defect in the hemostatic function. Furthermore, when fresh, healthy plasma was added to the Factor VII-deficient sample, the corresponding curve was close to the healthy curve, showing the sensor can detect the correction in hemostatic function that happens with the addition of plasma. Thus, FIG. 15 demonstrates the concept that the microsensor apparatus can identify a hemostatic dysfunction and the associated coagulopathy (curve 704), such as a deficiency in FVII or another coagulation factor based on detecting a prolonged $T_{peak}$ in a sample to which TF has been added. The apparatus may suggest a treatment that includes plasma (or a specific coagulation factor) or another treatment, which may include one or more bioactive agents, as disclosed herein, to restore the sample to a normal hemostatic function, as shown by curve 706 for the same FVII-deficient sample to which plasma has been added. In some examples, a plurality of different bioactive agents may be used to generate readout data, such as shown in the graph 700, and the agent (or combination of agents) that restores the sample closest to healthy blood (e.g., curve 702) can be identified (e.g., through an analysis function, such as error minimization) and presented on an output display of the device.

In view of the foregoing, devices and methods disclosed herein enable comprehensive hemostatic assessments at the point-of-injury, such as on a battlefield, or other location. This is accomplished by providing a versatile design that affords small "carry volume" for portability and rapid readout for guiding trauma-induced coagulopathy (TIC) mitigation at or near the point-of-injury. The portable device may be embodied as a miniaturized, multichannel, handheld, blood coagulation analyzer configured to implement dielectric spectroscopy as to provide rapid and comprehensive assessment of hemostatic status in TIC management to further guide intervention at the point-of-injury as well as in prolonged field care (PFC) settings.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to and the term "based on" means based at least in part on.

What is claimed is:

1. An apparatus, comprising:
   a dielectric microsensor comprising a microfluidic chamber that includes a capacitive sensing structure, the microfluidic chamber including a fluid input port adapted to receive a volume of a blood sample within the chamber, a bioactive agent being added to the blood sample, and the bioactive agent adapted to interact with at least a portion of the blood sample within the microfluidic chamber;
   a transmitter to provide an input radio frequency (RF) signal to an RF input of the dielectric microsensor;
   a receiver to receive an output RF signal from an RF output of the dielectric microsensor; and
   a computing device that computes dielectric permittivity values of the blood sample interacting with the bioactive agent within the microfluidic chamber over a time interval based on the output RF signal, the computing device to provide an assessment of hemostatic dysfunction based on the dielectric permittivity values.

2. The apparatus of claim 1, wherein the computing device is further programmed to identify at least one mechanism contributing to the hemostatic dysfunction.

3. The apparatus of claim 1, wherein the computing device is further programmed to determine and output a diagnosis describing the hemostatic dysfunction.

4. The apparatus of claim 1, wherein the computing device is further programmed to determine a therapy that is to be applied based on the dielectric permittivity values and provide an output specifying the determined therapy.

5. The apparatus of claim 4, wherein the determined therapy includes administration of a solution containing platelets, saline, recombinant fibrinogen, tranexamic acid, prothrombin complex concentrate, recombinant coagulation factors, plasma, or whole blood.

6. The apparatus of claim 1, wherein the capacitive sensing structure includes the bioactive agent disposed on a blood-contacting surface thereof.

7. The apparatus of claim 6, wherein the bioactive agent is adapted to interact deterministically with the blood sample received within the microfluidic chamber.

8. The apparatus of claim 1, wherein the dielectric microsensor comprising a plurality of microfluidic chambers, at least one of the plurality of microfluidic chambers including a predetermined bioactive agent disposed on a capacitive sensing structure thereof to interact with the volume of the blood sample received in the respective microfluidic chamber.

9. The apparatus of claim 8, wherein the computing device is further programmed to compute dielectric permittivity values for the blood sample in each of the microfluidic chambers over at least one time interval.

10. The apparatus of claim 9, wherein the computing device is further programmed to determine the assessment of hemostatic dysfunction and associated coagulopathy based on the dielectric permittivity values computed for the blood sample in at least two of the microfluidic chambers.

11. The apparatus of claim 9, wherein the computing device is further programmed to calculate a difference between the dielectric permittivity values computed for each of the microfluidic chambers and determine the assessment of hemostatic dysfunction and associated coagulopathy based on the difference.

12. An apparatus, comprising:
a dielectric microsensor comprising a microfluidic chamber that includes a capacitive sensing structure, the microfluidic chamber including a fluid input port to receive a volume of a blood sample within the microfluidic chamber, a bioactive agent disposed within the microfluidic chamber to interact with the volume of the blood sample received in the microfluidic chamber;
a transmitter to provide an input radio frequency (RF) signal to an RF input of the dielectric microsensor;
a receiver to receive an output RF signal from an RF output of the dielectric microsensor; and
a computing device that computes dielectric permittivity values of the blood sample that vary over a time interval based on the output RF signal, the computing device to provide an assessment of hemostatic dysfunction based on the dielectric permittivity values,
wherein the dielectric microsensor comprising a plurality of microfluidic chambers, at least one of the plurality of microfluidic chambers including a capacitive sensing structure having the bioactive agent disposed on surface thereof that is exposed within the respective chamber to interact with the volume of the blood sample received therein the respective microfluidic chamber, the capacitive sensing structure of at least one other of the plurality of microfluidic chambers having a non-functionalized surface that is exposed within the respective microfluidic chamber to contact the blood sample received therein the respective microfluidic chamber.

13. The apparatus of claim 1, wherein the capacitive sensing structure comprises:
a floating electrode disposed on surface of the microfluidic chamber;
a pair of sensing electrodes disposed on another surface of the microfluidic chamber opposite the floating electrode to provide a capacitive sensing area within the microfluidic chamber, the input RF signal provided to one of the sensing electrodes and the output RF signal being received from another of the sensing electrodes, wherein the bioactive agent is disposed on at least one of the electrodes.

14. The apparatus of claim 1, further comprising:
a housing that contains the transmitter, the receiver and the computing device; and
a sensor interface including electrical contacts configured to connect to the dielectric microsensor for communicating the input RF signal and the output RF signal.

15. The apparatus of claim 1, wherein the bioactive agent is adapted to promote, accelerate, or inhibit coagulation of the blood sample.

16. A method, comprising:
introducing a volume of at least one blood sample into a chamber between electrodes of a dielectric microsensor, a bioactive agent being added to the blood sample, and the bioactive agent interacting with the blood sample within the chamber;
providing an input radio frequency (RF) signal to an input of the dielectric microsensor;
receiving an output RF signal from an output of the dielectric microsensor in response to the input RF signal, the output RF signal representing a measure of impedance of a volume of the blood sample disposed in the dielectric microsensor according to the interaction with the bioactive agent within the chamber;
calculating dielectric permittivity values of the blood sample over a measurement time interval based on the output RF signal; and
providing an assessment of hemostatic dysfunction based on analysis of the dielectric permittivity values.

17. The method of claim 16, wherein introducing the volume further comprises introducing a volume of blood into each of a plurality of microfluidic chambers, each of the plurality of microfluidic chambers including a capacitive sensing structure having an unmodified surface or a uniquely functionalized surface containing a quantity of a respective bioactive agent to interact with the blood sample responsive to the blood sample being introduced within the respective microfluidic chamber.

18. The method of claim 17, wherein dielectric values are computed for each of the microfluidic chambers.

19. The method of claim 18, wherein the assessment of hemostatic dysfunction is determined based on the dielectric permittivity values computed for at least two of the microfluidic chambers.

20. The method of claim 19, further comprising computing a difference between dielectric permittivity values for at least some of the microfluidic chambers and determining the assessment of hemostatic dysfunction and associated coagulopathy based on the computed difference.

21. The method of claim 16, further comprising generating an output that specifies a therapy to administer based on the assessment of hemostatic dysfunction and associated coagulopathy.

22. The method of claim 21, wherein the therapy includes one of a solution containing platelets, saline, recombinant fibrinogen, tranexamic acid, prothrombin complex concentrate, recombinant coagulation factors, plasma, or whole blood.

23. The apparatus of claim 1, wherein the bioactive agent comprises at least one of collagen, fibrinogen, inorganic polyphosphate (PolyP), chitosan, kaolin, phosphatidylserine (PS), Adenosine 5'-diphosphate (ADP), thrombin receptor-activating peptide (TRAP), aprotinin, tranexamic acid, or Tissue Factor (TF).

24. The method of claim 16, wherein the bioactive agent comprises at least one of collagen, fibrinogen, inorganic polyphosphate (PolyP), chitosan, kaolin, phosphatidylserine (PS), Adenosine 5'-diphosphate (ADP), thrombin receptor-activating peptide (TRAP), aprotinin, tranexamic acid, or Tissue Factor (TF).

25. The apparatus of claim 1, wherein the bioactive agent is disposed in the chamber prior to introducing the blood sample or the bioactive agent is introduced into the chamber concurrently with the blood sample.

26. The apparatus of claim 1, wherein the bioactive agent is disposed on one or more surfaces within the chamber.

27. The method of claim 16, wherein the bioactive agent is disposed in the chamber prior to introducing the blood sample or the bioactive agent is introduced into the chamber concurrently with the blood sample.

28. The method of claim 16, wherein the bioactive agent is disposed on one or more surfaces within the chamber.

29. The method of claim 16, wherein the bioactive agent is adapted to promote, accelerate, or inhibit coagulation of the blood sample.

* * * * *